United States Patent [19]

Barnes et al.

[11] Patent Number: 5,496,996
[45] Date of Patent: Mar. 5, 1996

[54] PHOTOELECTRIC DEVICE WITH CAPABILITY TO CHANGE THRESHOLD LEVELS IN RESPONSE TO CHANGING LIGHT INTENSITIES

[75] Inventors: Kenneth F. Barnes; Hongzhi Kong, both of Freeport, Ill.

[73] Assignee: Honeywell Inc., Minneapolis, Minn.

[21] Appl. No.: 378,134

[22] Filed: Jan. 24, 1995

[51] Int. Cl.⁶ ..................................................... G01N 9/04
[52] U.S. Cl. ...................................... 250/223 B; 356/240
[58] Field of Search ........................... 250/223 B, 222.1, 250/222.2, 221, 223 R, 559.4, 559.24; 340/555–557; 356/429–430, 240, 384–386

[56] References Cited

U.S. PATENT DOCUMENTS

| | | | |
|---|---|---|---|
| 5,008,531 | 4/1991 | Ono et al. | 250/22.1 |
| 5,008,532 | 4/1991 | Ono et al. | 250/222.1 |
| 5,301,129 | 4/1994 | McKaughan et al. | 356/430 |
| 5,318,172 | 6/1994 | Kenny et al. | 250/223 B |

*Primary Examiner*—Edward P. Westin
*Assistant Examiner*—Que T. Le
*Attorney, Agent, or Firm*—William D. Lanyi

[57] ABSTRACT

A photoelectric sensor is provided with the capability of calculating a threshold magnitude based on a maximum light intensity received by a light sensitive device. The maximum value of the light intensity is determined during a preselected period of time when no object is blocking the path of a light beam. A second threshold magnitude is used to assist the present invention in determining the leading edge and trailing edge of a transparent object. The values of the first and second threshold magnitudes are updated dynamically as bottles pass through the path of the light beam. This permits the photoelectric sensor to react to changes in light intensity without providing false signals of bottles within the light path or missing bottles that are within the light path.

14 Claims, 20 Drawing Sheets

PHOTOELECTRIC DEVICE WITH CAPABILITY TO CHANGE THRESHOLD LEVELS IN RESPONSE TO CHANGING LIGHT INTENSITIES

BACKGROUND OF THE INVENTION

1. Field of the Invention

The present invention relates generally to photoelectric devices that are used to detect the presence of objects which obstruct a beam of light and, more particularly, to a photoelectric system that is capable of changing a threshold magnitude in response to changes in light intensity of a light beam when no objects are obstructing the beam.

2. Description of the Prior Art

Many photoelectric detection systems are known to those skilled in the art. In a typical photoelectric detection system, a light source is provided which directs a beam of light that is received by a light sensitive component. For example, a light emitting diode can be used as a light source and a photodiode or phototransistor can be used as the light sensitive component. The light sensitive component can be configured within a separate housing and disposed so that a beam of light is directed from a first housing with the light emitting diode within it to a second housing with the photosensitive component in it or the light emitting diode and the photosensitive component can be disposed within a common housing. In this later type of photoelectric device, a reflector can be used to receive the light beam from the light source and reflect it back toward the light sensitive component. In typical sensors of this type, a received light signal is compared with a preselected fixed threshold magnitude. If the receiving signal is less than the threshold, the presence of an object is detected. On the otherhand, if the signal is greater than the threshold, the sensor determines that no object is present in the path of the light beam. Therefore, a threshold must be selected in such a way that its magnitude is less than the signal level when no object is obstructing the beam path but greater than the signal level when an object is obstructing the beam path. If the system is intended to detect opaque objects, a threshold can be preselected and set to a value that is a very small percentage of the unobstructed light beam intensity. If the photoelectric system is intended to detect the presence of transparent objects, such as clear glass or plastic bottles, this type of preselected threshold can be severely disadvantageous. Since transparent objects decrease the intensity of light received by the light sensitive component by a relatively small amount, the preselected threshold must be set to a value that is almost equal to the unobstructed light beam intensity. This creates a situation in which changes in the transmitted light intensity can product false signals even when no object obstructs the light beam.

U.S. Pat. No. 5,008,531, which issued to Ono et al on Apr. 16, 1991, discloses a pulsed light identifying system which includes a photoelectric conversion unit for receiving a pulsed light from a light emitting part of a light receiving part to generate a light reception signal that varies in magnitude according to the quantity of the received light. A peak holding circuit is provided with a time constant that is relatively long in comparison with the pulse interval of the pulsed light. The peak holding circuit stores a peak value of the light reception signal for its time constant. The peak value is divided by a constant for application to a comparator. The comparator compares it with the light reception signal as a threshold. A peak value of the light reception signal is held and the peak value thus held is specified as a threshold to the light reception signal. Therefore, in the event of a decrease in the quantity of emitted light due to a secular change or of decrease in the quantity of received light due to mist and oil film, the threshold decreases accordingly.

U.S. Pat. No. 5,008,532, which issued to Ono et al on Apr. 16, 1991, discloses a light reception signal circuit for a photoelectric switch. The circuit includes a photoelectric conversion circuit for receiving light from a light emitting part controlled for periodic emission. The photoelectric conversion circuit generates an electrical signal corresponding to the quantity of the received light. A programmable attenuator receives the output electrical signal and attenuates it in even step in response to a digital control signal. A first comparator compares the output voltage with a predetermined upper bound threshold. The first comparator generates a clock signal when the output voltage exceeds the upper bound threshold. A peak holding circuit for receiving an output voltage of the programmable attenuator holds the peak value of the output voltage on a time constant that is much longer than an emission period of the light emitting part. A second comparator compares the output voltage of the peak holding circuit with a predetermined lower bound threshold and generates an outgoing signal when the output voltage decreases below the lower bound threshold. A counter counts the clock pulses thereby generating a digital control signal for increasing the attenuation of the programmable attenuator. A third comparator compares the output voltage of the programmable attenuator with a predetermined decision level to produce the detection output of the photoelectric switch.

SUMMARY OF THE INVENTION

The present invention provides a photoelectric sensor that comprises a light source which can be a light emitting diode. It also comprises a light sensitive device that provides a first signal which is representative of an intensity of light imposed on the light sensitive device. The light sensitive device is disposed at a position to receive a beam of light from the light source. In a preferred embodiment of the present invention, the sensor also comprises a means for comparing the first signal to a threshold magnitude in order to detect the presence of an object in the path of the light beam.

A preferred embodiment of the present invention also comprises a first means which is connected in signal communication with the light sensitive device for determining an updated value of the threshold magnitude as a function of the maximum value, or peak value, of a magnitude of the intensity of light imposed on the light sensitive device during a first preselected period of time. It also comprises a means for deactivating the first determining means during a second preselected period of time. The present invention further comprises a means for replacing a previous value of the threshold magnitude with an updated value of the threshold magnitude upon the initial detection of an object in the path of the light beam.

In a particularly preferred embodiment of the present invention, the sensor further comprises a means for providing a second signal when the first signal achieves a first relationship with the first threshold magnitude. A particularly preferred embodiment of the present invention further comprises a second means for determining a second threshold magnitude as a function of the first threshold magnitude. In an embodiment of this type, the first signal is compared to the first threshold magnitude to detect a leading edge of an object and the first signal is compared to the second threshold magnitude to detect a trailing edge of the object.

One embodiment of the present invention comprises a means for training the sensor to recognize the absence of an object in the path of the light beam and determine the first threshold magnitude without the object in the path. Although the present invention is operable in several modes of configuration, one embodiment of the present invention comprises a reflector that is disposed to receive the beam of light from the light source and reflect it toward the light sensitive device. In this embodiment, the light source and the light sensitive device are typically disposed within a common housing. The first and second determining means of the present invention can comprise a microprocessor although this configuration is not a requirement.

In certain embodiments of the present invention, a photoelectric sensor is provided with a floating reference which changes in relation to changes in the light intensity received by a light sensitive component which are due to reasons other than the actual presence of an object within the path of a light beam. When the light signal received by the light sensitive component experiences a change in intensity, a threshold magnitude is automatically updated so that a relative relationship between a peak light intensity value and the threshold magnitude remains constant. Because of this characteristic of the present invention, the photoelectric sensor can detect an object which is transparent without requiring manual adjustments of the threshold magnitude.

In a particularly preferred embodiment of the present invention, a photoelectric sensor is provided with the ability to learn certain capabilities. This characteristic allows the sensor to set proper reference levels and threshold magnitudes after a number of objects pass through the light beam. This feature also permits the sensor to exhibit a self recovery mode of operation in response to certain fault conditions.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Figure 1:
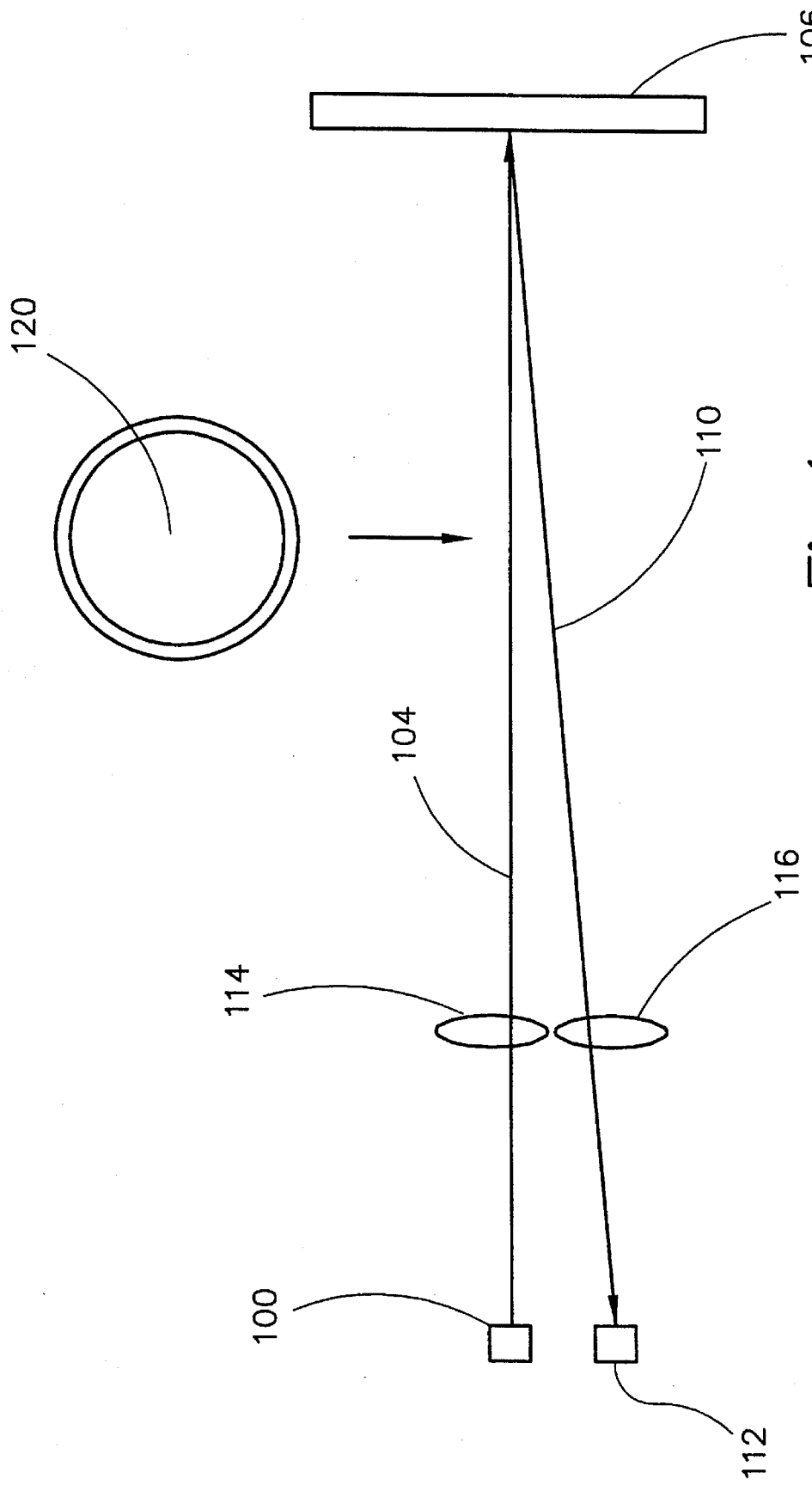
FIGS. 1 and 2 show the general set up of a photoelectric sensor for the purpose of detecting an object passing through a light beam.

Throughout the Description of the Preferred Embodiment, like components will be identified by like reference numerals. The present invention will be described below in terms of its application in conjunction with a photoelectric sensor. However, it should be understood that the present invention can be used in conjunction with virtually any type of radiation. The radiation does not have to be light in all embodiments of the present invention. Ultrasonic sensors, for example, could implement the concepts of the present invention. The techniques of the present invention can be applied to any type of sensor that incorporates a radiation source and a radiation sensitive device which are used in combination with each other to detect the passage of an object through a beam of radiation traveling from the radiation source to the radiation sensitive device.

FIG. 1 illustrates a highly schematic representation of a photoelectric device associated with a reflector to detect the presence of an object. In an arrangement of this type, a light source 100, which can be a light emitting diode, is provided to direct a beam of light 104 toward a reflector 106. A reflected beam of light 110 is directed back toward a light sensitive device 112. In typical application of this type, lenses, 114 and 116 are used to collimate and focus the light beams, respectively. The arrangement is typically configured so that an object 120 can pass in a direction which can obstruct the path along which the light beams pass.

Figure 2:
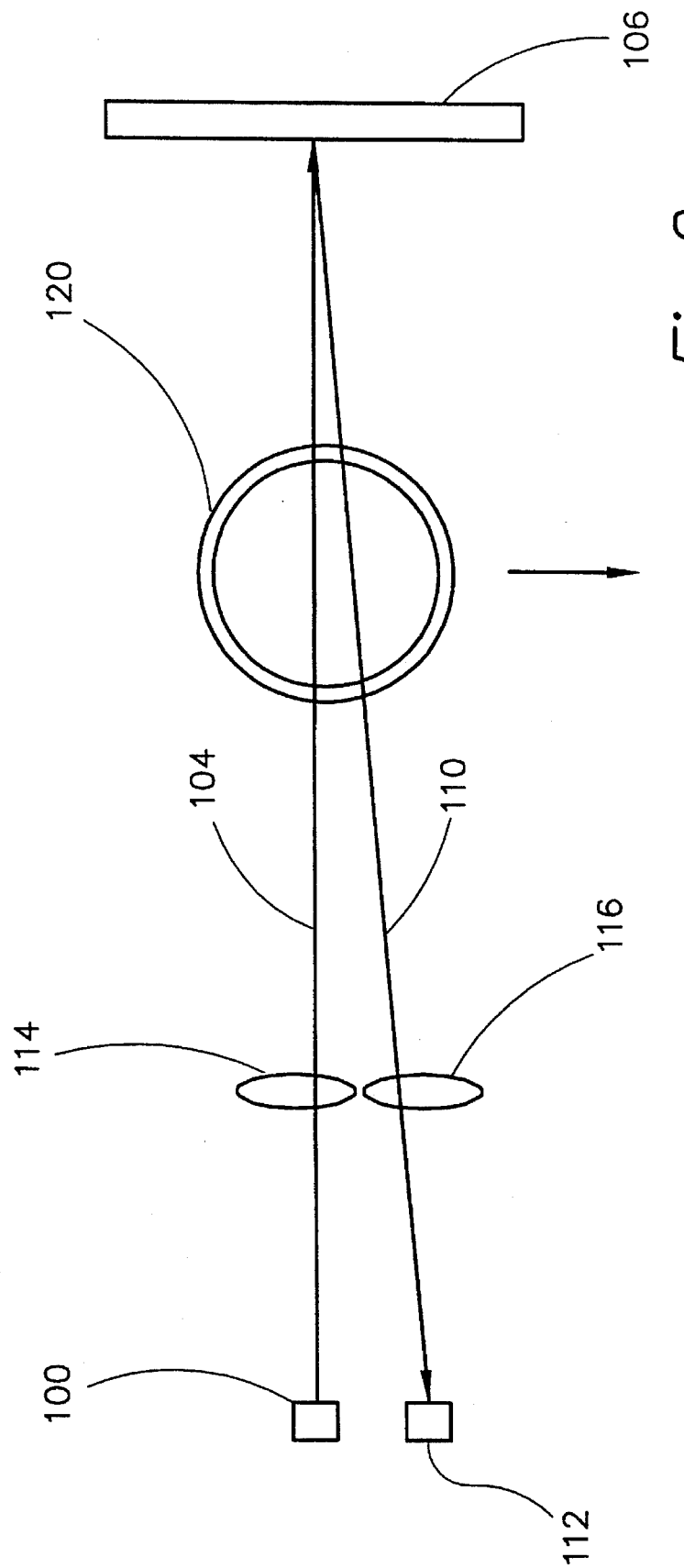
Figure 3:
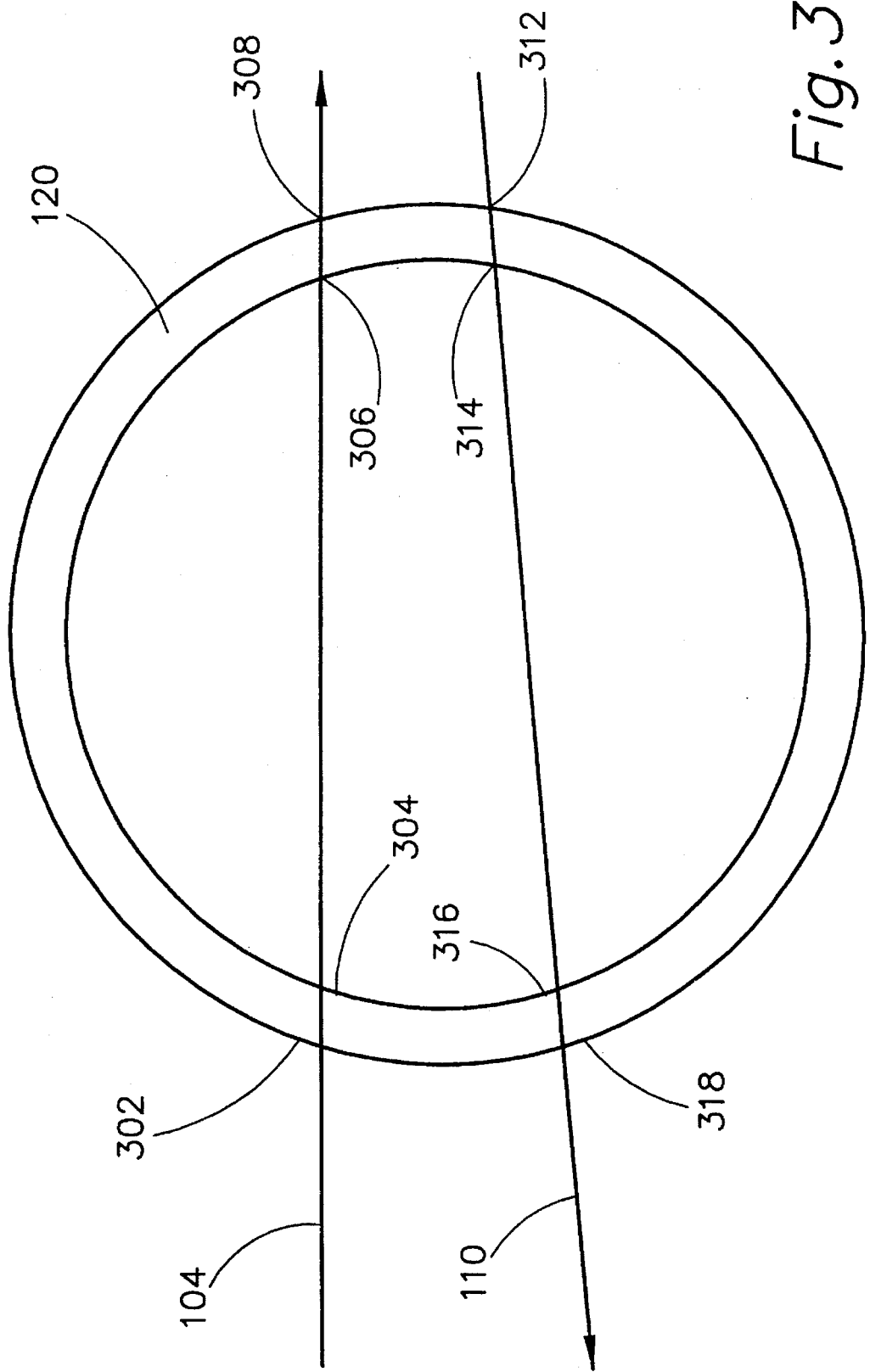
FIG. 3 is an enlarged view of a transparent object passing through a light beam.

FIG. 2 illustrates the configuration of FIG. 1 wherein the object 120 has moved to a location where it obstructs the path of the light beam, 104 and 112. When this movement of the object 120 occurs, the intensity of light received by the light sensitive device 112 is diminished. This decrease in the magnitude of light received by the light sensitive device 112 can be used to indicate the presence of an object in the path of the beam of light. FIG. 3 is an expanded view of the object 120 and the light beams, 104 and 110, as illustrated in FIG. 2. If the object 120 is transparent, the decrease in light received by the light sensitive device is diminished, but not totally obliterated as it would be if the object was opaque. The transmitted light beam 104 is slightly reflected by the first surface 302 and again by the second surface 304 of the transparent object 120 which can be a glass or clear plastic bottle. The transmitted light beam 104 is again reflected as it passes through surfaces 306 and 308. After the light beam is reflected by the reflector 106, the reflected light beam 110 passes through surfaces 312, 314, 316 and 318 as illustrated in FIG. 3. If the object 120 is highly transparent, the total decrease in the intensity of light of the beam after it has passed through the bottle in both directions as illustrated in FIG. 3 can be as low as 28% due to Fresnel reflection loss only.

Figure 4:
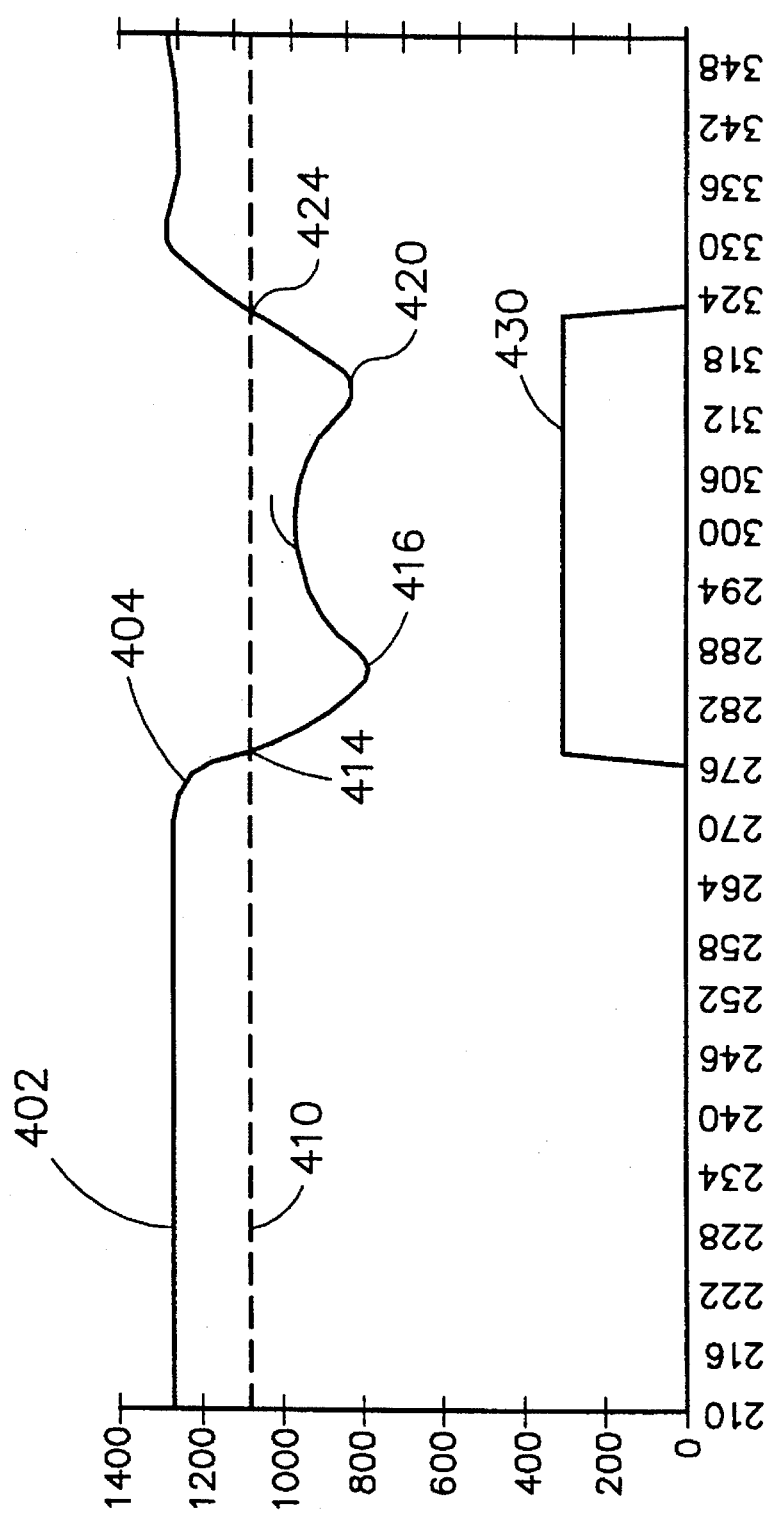
FIG. 4 is a curve of empirical data showing the light signal changes caused by a single transparent object.

In order to describe the operation of photoelectric devices that are used to detect transparent objects and in order to further describe the situation in which the present invention is intended for use, FIG. 4 is provided. FIG. 4 represents actual empirically derived data of the light intensity received by the light sensitive device as a transparent object passes into the path of the light beam. The vertical axis represents digital values of light intensity and the horizontal axis represents a time sequence. The light signal 402, when the light beam in unobstructed by any object, has an intensity of approximately 1250 units. As a transparent object moves into obstructing relationship with the light beam, this signal begins to decrease at point 404. If a threshold magnitude 410 is used as a comparison with the light signal 402, the decrease in the intensity of the light signal 402 can be used to indicate the presence of an object in the light path. When the light signal 402 decreases to a magnitude which is less than the threshold 410, as is indicated by point 414, a transparent object can be indicated. When the light signal first passes through the leading edge of the bottle, the maximum decrease in light intensity occurs. This is represented by point 416. When the bottle passes to a position as indicated in FIGS. 2 and 3, slightly more light can be received by the light sensitive device and the signal rises to point 418. When the bottle proceeds to a position where its trailing edge blocks the light path, the signal again diminishes to point 420. Point 424 in FIG. 4 indicates the passage of the bottle out of an obstructing relationship with the light beam. A second signal that is provided by the photoelectric sensor is represented in FIG. 4 and identified by reference numeral 430. The rising and falling edges of signal 430 can be made to coincide with the intersection between signal 402 and threshold 410 in a simplified system. However, as will be described in greater detail below, the present invention provides a much more sophisticated means for providing signal 430.

Figure 5:
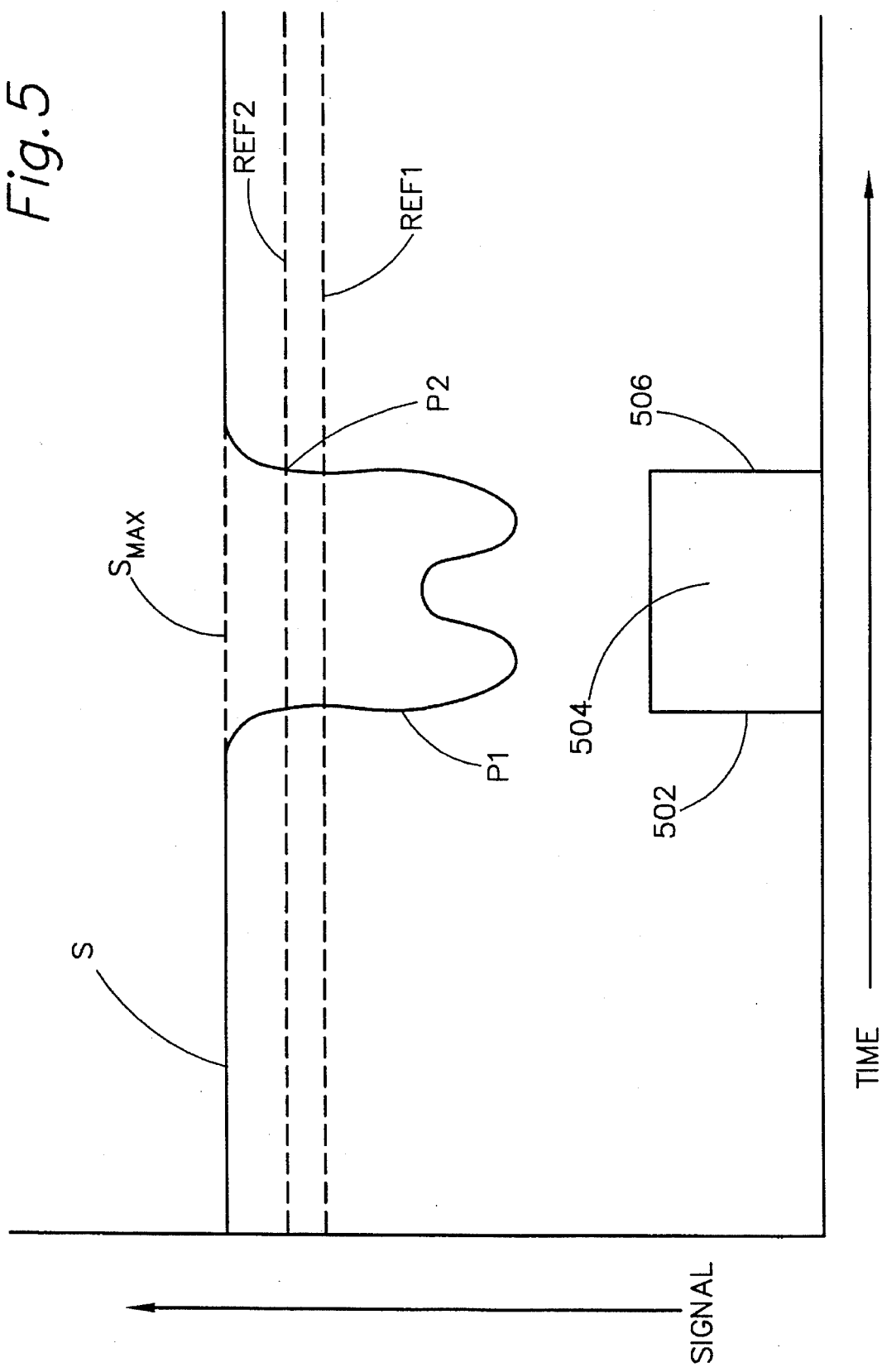
FIG. 5 is a representation of the signal shown in FIG. 4.

As described above, FIG. 4 represents actual empirical data of a light signal 402 as a clear bottle passes through the light beam. FIG. 5, on the other hand, is a hypothetical representation of a similar signal that will be used herein to discuss the disadvantages of the prior art and the advantages of the present invention.

FIG. 5 illustrates a signal S that is compared with two reference values. A first threshold magnitude REF1 is calculated as a function of the maximum signal $S_{MAX}$. A second threshold magnitude REF2 is determined as a function of the first threshold magnitude REF1. When the signal drops to a value which is less than the first threshold magnitude REF1, as indicated by point P1, a rising edge 502 of a second signal 504 is provided. The falling edge 506 of the second signal 504 is provided when the light signal S rises to a point that is greater than the second threshold magnitude REF2. Although the second threshold REF2 is typically set to a value which is approximately three percent greater than the first threshold magnitude REF1, it should be clearly understood that this relative difference is not limiting to the present invention. In fact, the difference in value between the first and second threshold magnitudes is chosen in response to potential electrical noise in the signals and can be very significantly, depending on the particular application in which the present invention is used. In a perfectly noise free environment, the first and second threshold magnitudes could actually be equal to each other with no hysteresis being required.

Figure 6:
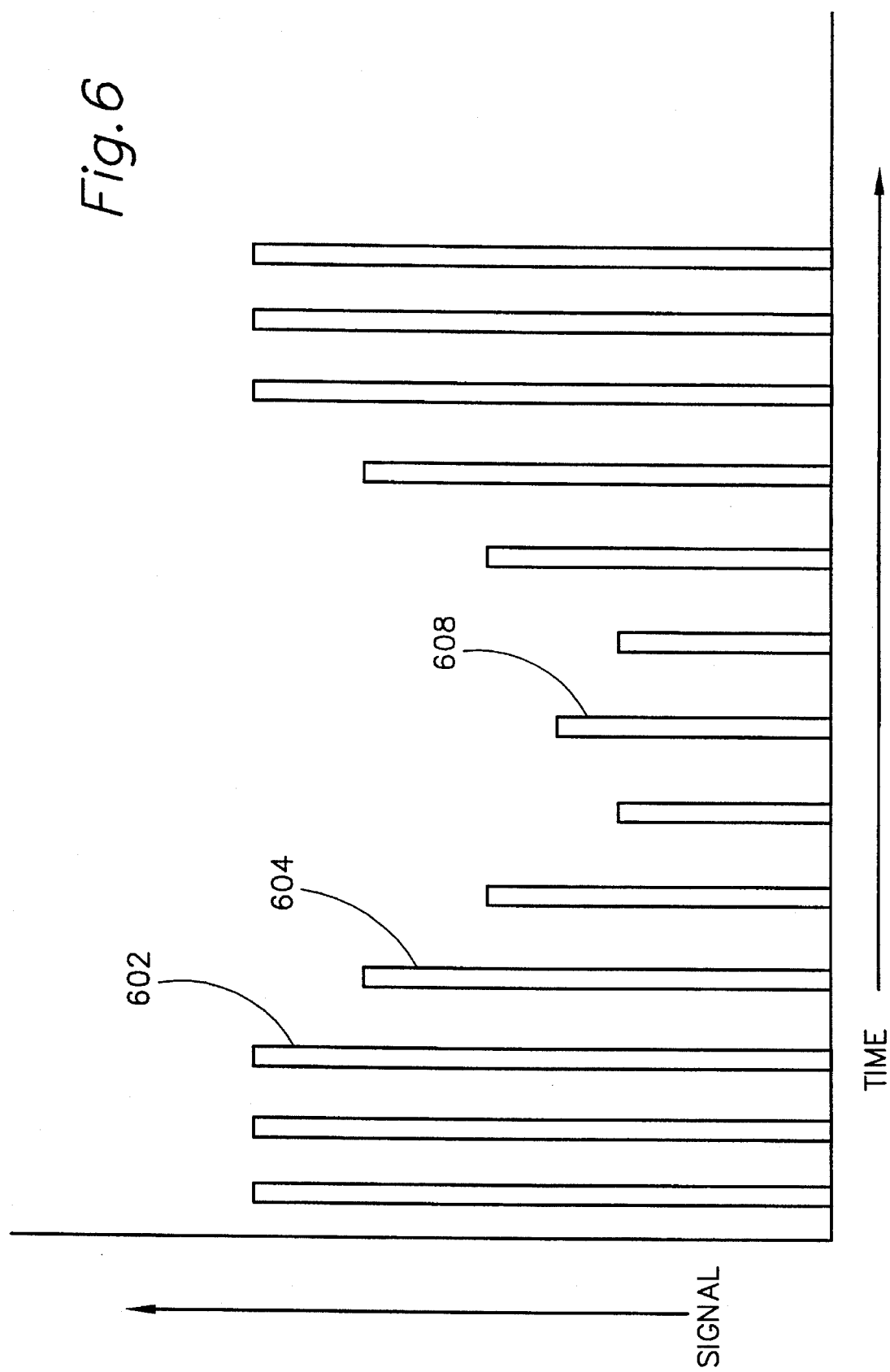
FIGS. 6 and 7 show pulsed signals received by a light sensitive device.
Figure 7:
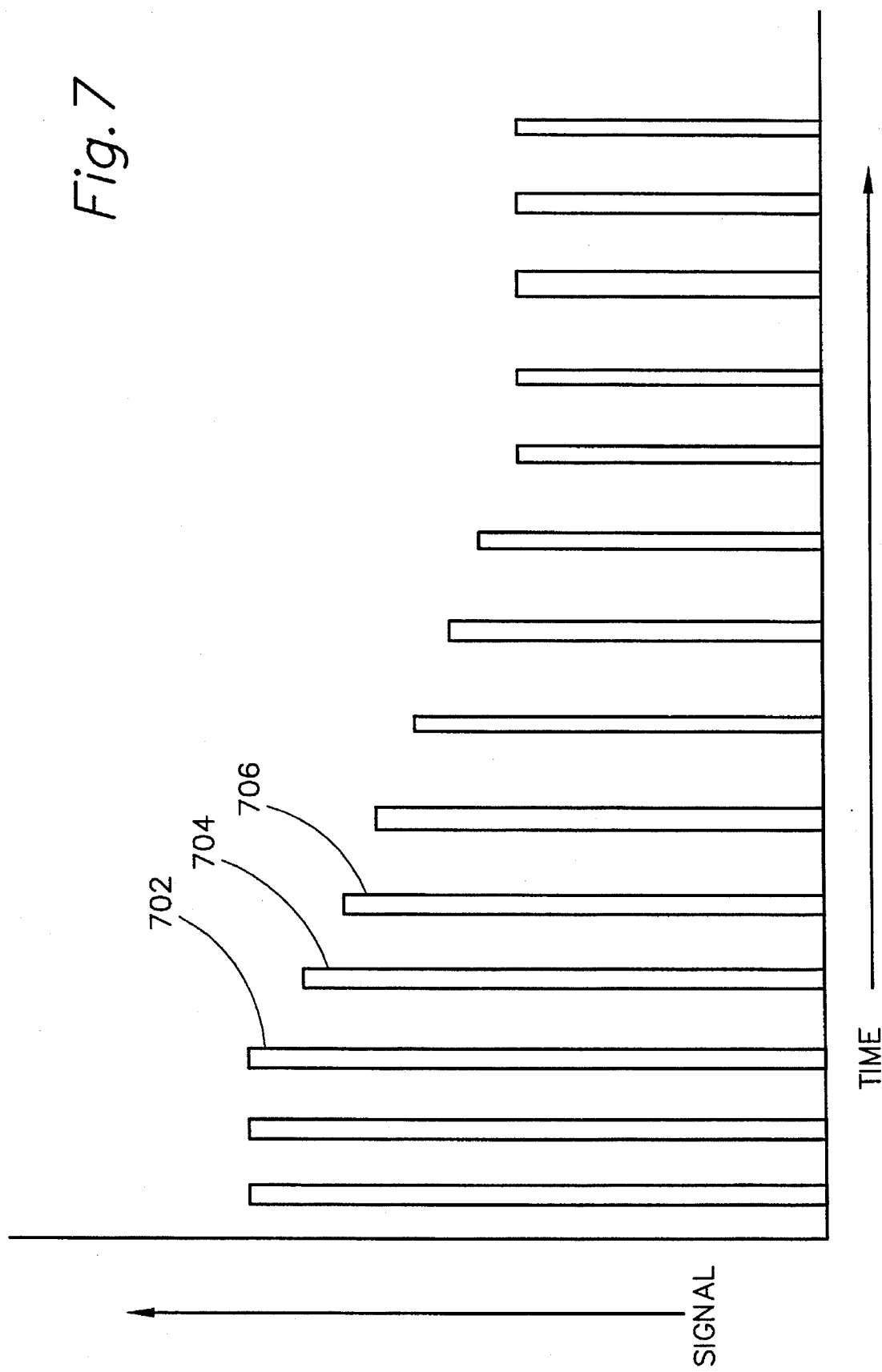

Known devices use thresholds which are determined as a function of the maximum signal $S_{MAX}$. One such system is described in the Ono et al patent above. Before describing the significant disadvantages of the prior art systems, it is important to understand that most photoelectric sensors use pulsed light signals rather than a continuous beam of light. FIGS. 6 and 7 are provided to illustrate this type of signal transmission and how it relates to photoelectric sensors and their possible disadvantages.

FIG. 6 illustrates a plurality of light pulses that correspond generally to the signals represented by line drawings in FIGS. 4 and 5. As can be seen in FIG. 6, the intensity of light pulse 604 is less than the intensity of light pulse 602. These intensities continue to decline as the leading edge of a bottle passes in obstructing relationship with the light beam. As discussed above in relation to FIG. 4, the slight increase in light intensity represented by light pulse 608 indicates the general center of a transparent bottle. As the bottle passes out of obstructing relationship with the light beam, the intensity of the light signals increases. The similarity in general shape of the group of light pulses in FIG. 6 and the line configuration of FIG. 5 can be seen. One problem that can be encountered in systems like those described above is that the intensity of light can decrease even when no object blocks the path of light. This could occur if the atmosphere surrounding the system becomes smoky or if a water mist exists in the region of the light beam. Those skilled in the art of photoelectric sensors and their applications will realize that the changes in light intensity described herein can also be caused by temperature changes which affect the operation of both the light emitting diode and the light detector, dust particles in the atmosphere, moisture in the atmosphere and many other types of contamination. Furthermore, liquid can be sprayed on the reflector or on the lenses of the photoelectric device. FIG. 7 represents the intensity of light received by the light sensitive device when no obstructing objects are within the path of the light beam. The intensity of light is shown decreasing as time passes. Light pulse 704 is less than light pulse 702 and, similarly, light pulse 706 is less than light pulse 704. If no corrective action is taken immediately upon the decrease in the light intensity, the presence of objects in the path of the light beam can be falsely indicated. Alternatively, false signals can be transmitted from the photoelectric sensor that indicate the absence of an object in the path of the light beam when an object is actually present.

Figure 8:
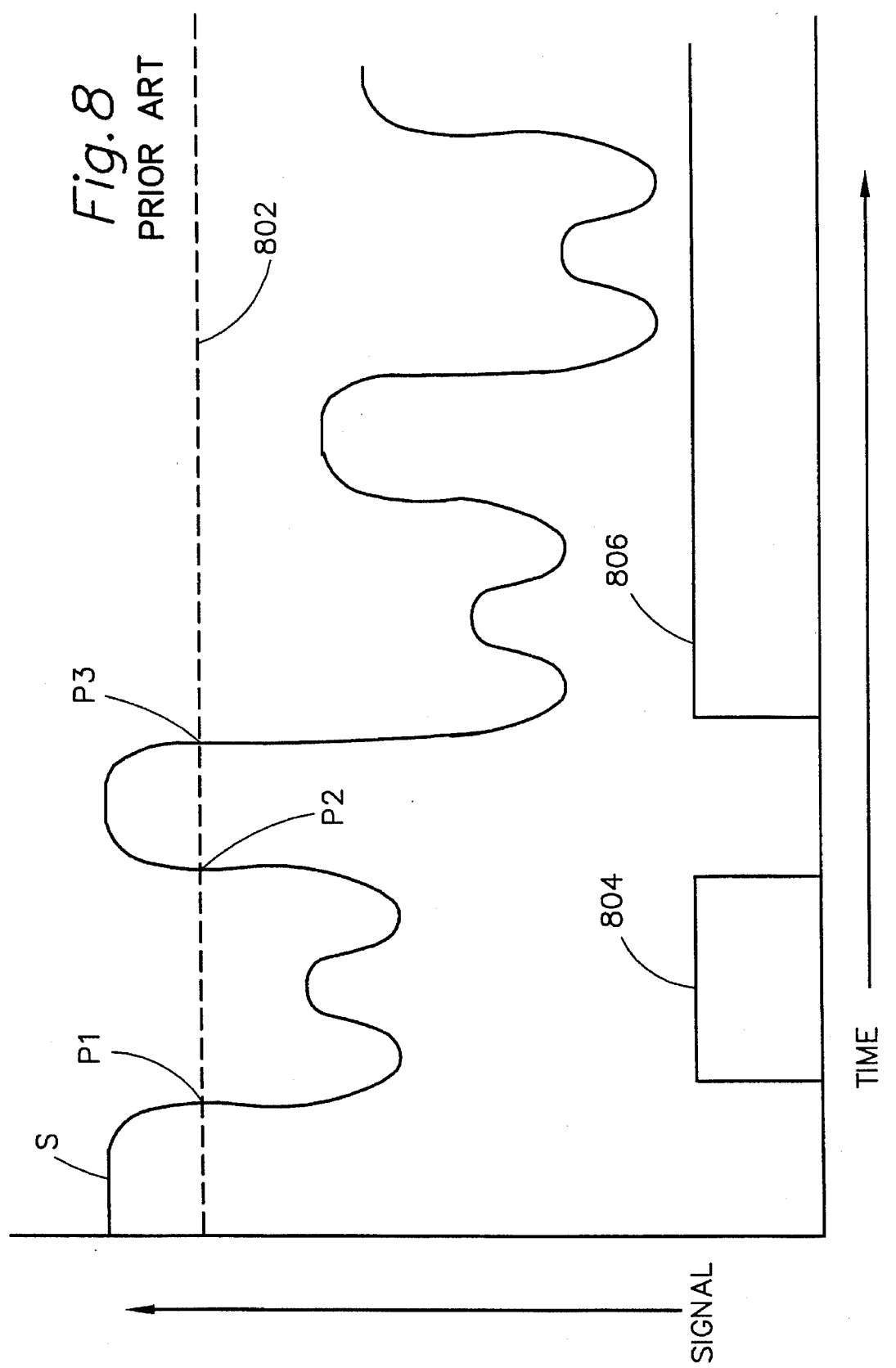
FIG. 8 represents a problem condition for a light detector.

FIG. 8 is intended to represent a situation wherein a light detector provides an improper signal in response to a decrease in the light received by the light sensitive device. Signal S represents the intensity of light received by the light sensitive device. If a single threshold 802 is used by the system and the threshold is not properly updated periodically, a decrease in light intensity can result in false signals from the detector. At the beginning of the time cycle represented in FIG. 8, the signal S decreases to a value that is less than the threshold 802 at point P1. This results in the rising edge of the second signal 804. When the signal increases at point P2 to a value that is greater than the threshold 802, the falling edge of the second signal 804 is provided. This represents a proper operation of the device. However, after point P2, the light intensity begins to decrease. At point P3, the light intensity is still sufficient to trigger the rising edge of the second output signal 806. However, as the light intensity of signal S continues to decline, the light following the trailing edge of the second bottle represented in FIG. 8 is insufficient to rise to a magnitude greater than the threshold magnitude 802. As a result, the falling edge of the second output signal 806 is not transmitted because signal S does not rise to a sufficient magnitude which is greater than threshold magnitude 802 as required. Therefore, the passage of the second and third bottles in FIG. 8 is not properly detected and, instead, a continuous output signal 806 is erroneously provided.

Figure 9:
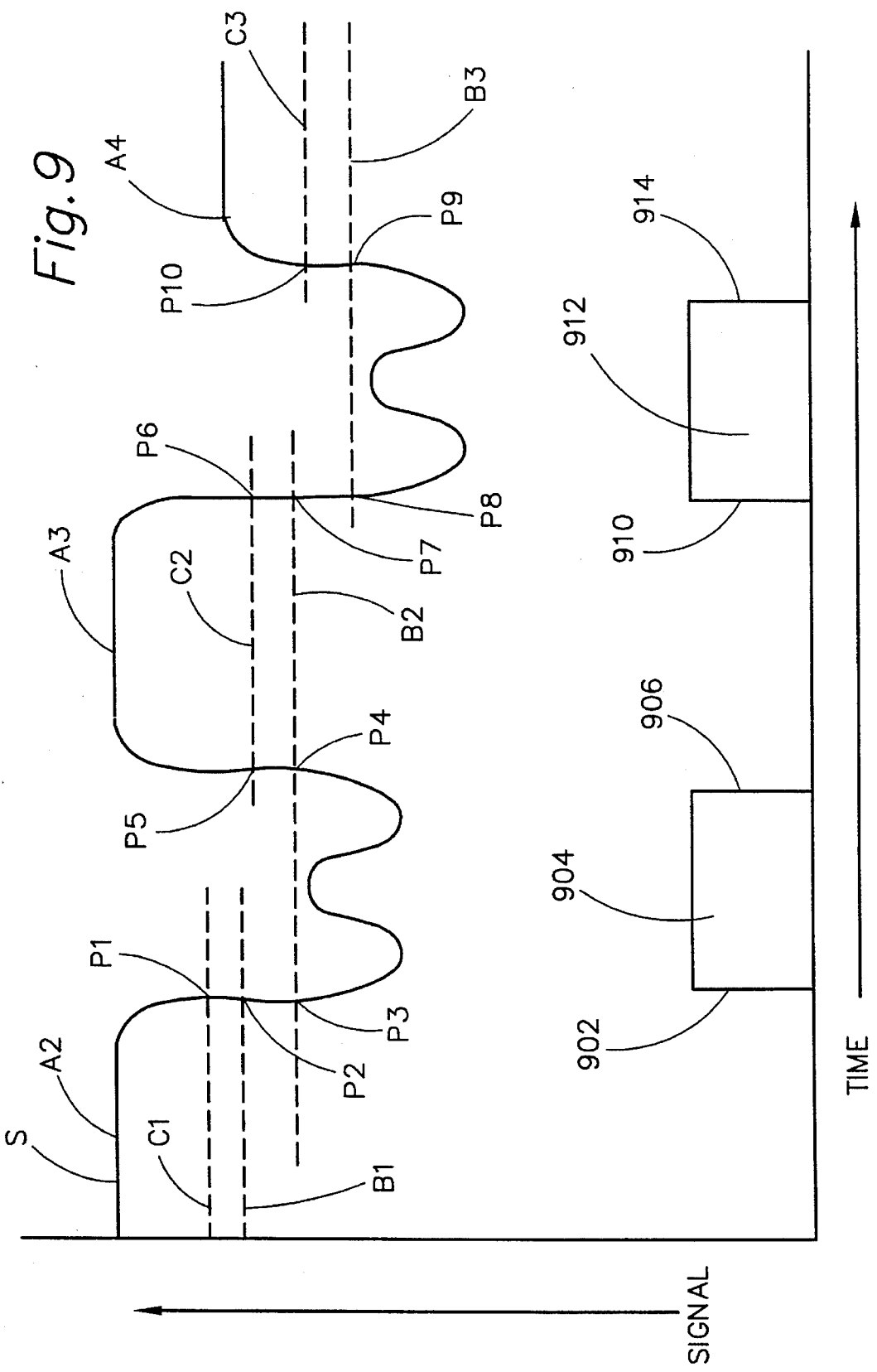
FIG. 9 shows the operation of the present invention.

FIG. 9 illustrates the reaction of the present invention to a circumstance where the signal S gradually decreases over time. It should be understood that reference numeral A1 is not shown. However, it should further be understood that a previously determined maximum value of signal S had been measured and stored prior to the period of time represented in FIG. 9. Based on that previously determined maximum value A1, a first threshold magnitude B1 was determined. A second threshold magnitude C1 was then determined as a function of the first threshold magnitude B1. It should be clearly understood that the reason for providing a second threshold magnitude is to assure a certain degree of hysteresis. As discussed elsewhere in this description of the present invention, the hysteresis would not be needed if there is no possibility of electrical noise in the signals. However, in actual applications, a certain amount of electrical noise is to be expected and, therefore, the first and second threshold magnitudes will be different from each other to account for this possibility. During the initial period of time represented by FIG. 9, the maximum values of the signal are continuously monitored and a representative maximum value, that will be used as a reference, is stored as A2. However, no calculation of threshold magnitude is immediately made as a function of the maximum value A2 until the signal S decreases to a value that is less than the previously determined first threshold magnitude B1. Proceeding chronologically with the signal S as it begins to decrease from the point identified as A2 in FIG. 9, the magnitude of signal S drops below the second threshold magnitude C1. This occurrence, identified as point P1, is ignored by the present invention. When the signal further drops to a value which is less than the first threshold magnitude B1, as indicated by point P2, the present invention stops monitoring the maximum magnitudes of signal S and no longer calculates new values for the maximum value A2. Instead, at point P2 the present invention calculates a new first threshold B2 as a function of the maximum value A2. It also calculates a new value of the second threshold magnitude C2 as a function of the first magnitude B2. When the signal S drops to a value which is less than the updated value of the first threshold magnitude B2, the rising edge 902 of the second signal 904 is provided. The second signal 904 is the output signal of the present invention which indicates that a bottle is present within the path of the light beam. Proceeding chronologically, the signal S eventually rises to a point that is greater than the updated value of the first threshold magnitude B2. This is represented as point P4 in FIG. 9. This occurrence is ignored by the present invention. When the signal S continues to rise, it eventually achieves a value that is greater than the second threshold magnitude C2. This is indicated as point P5 in FIG. 9. When this occurs, the falling edge 906 of the second signal 904 is provided. This indicates that the bottle has passed out of obstructing relationship with the light beam path. Point P5 is used by the present invention to again begin monitoring signal S for a new maximum value. This occurs during the time period identified by reference numeral A3. During that preselected period of time, the present invention monitors signal S to determine the maximum value of signal S during the preselected period of time between the existence of bottles in the light path.

With continued reference to FIG. 9, it can be seen that between points P2 and P5, the present invention does not monitor the value of signal S in the determination of new maximum values. It should also be understood that the maximum value determination for value A2 is separate from the determination for value A3. These are separate monitoring steps of the present invention.

When signal S proceeds chronologically to the point identified as P6, it falls to a value which is less than the second threshold magnitude C2. This occurrence is ignored by the present invention. When the signal S eventually falls to a value that is less than the first threshold magnitude B2, the present invention uses the maximum reference value A3 that was previously determined and calculates a new and updated first threshold magnitude B3 as a function of A3. However, the present invention does not immediately indicate the presence of a bottle in the light path. When signal S continues to fall to a value that is less than the updated threshold magnitude B3, as indicated by point P8, the leading edge 910 of a new second signal 912 is provided. Continuing chronologically, the light signal eventually rises to a value that is greater than the new threshold magnitude B3. This occurs at point P9. This occurrence is ignored by the present invention. When the signal eventually arises above the value of the second threshold magnitude C3, as indicated by point P10, the present invention again begins to search for new maximum values A4.

With continued reference to FIG. 9, it should be understood that at points P2 and P7 the present invention stops monitoring signal S for new maximum values. It begins monitoring for maximum values at points P5 and P10. When the signal S rises to a value that is greater than the second threshold magnitude C3, the falling edge 914 of the second signal 912 is provided. As can be understood from the description above and the illustration in FIG. 9, the present invention selectively monitors for maximum values of signal S between bottles as determined by the relative magnitudes of signal S and the first and second threshold magnitudes. It stops monitoring maximum values during the period of time when bottles are passing through the light beam. By observing the relative magnitudes of the threshold magnitudes identified as B1, B2 and B3, it can be seen that the first threshold magnitude is continually decreased as the maximum values of signal S decrease. This allows the present invention to react immediately to changes in the intensity of light received by the light sensitive device when bottles are not present within the path of the light beam.

With continued reference to FIG. 9, it should be understood that all of the values represented by line S are actually individual data points as described above in conjunction with FIGS. 6 and 7. Each of the data points is the average of a preselected number of received data points from the light sensitive device. These raw signals are stored and a moving average of a preselected number of previous signals is used to provide the signals that are analyzed by the present invention. This smoothing technique prevents the possible aberrations that could result from electrical noise. In addition, the maximum reference magnitudes, A2, A3 and A4, are actually the moving averages of a preselected number of previously measured maximum values. The actual numbers of values used in these moving averages can be selected to provide the appropriate smoothing of the signals while avoiding undue delay in the reaction time of the present invention to changing magnitudes of signal S.

Figure 10:
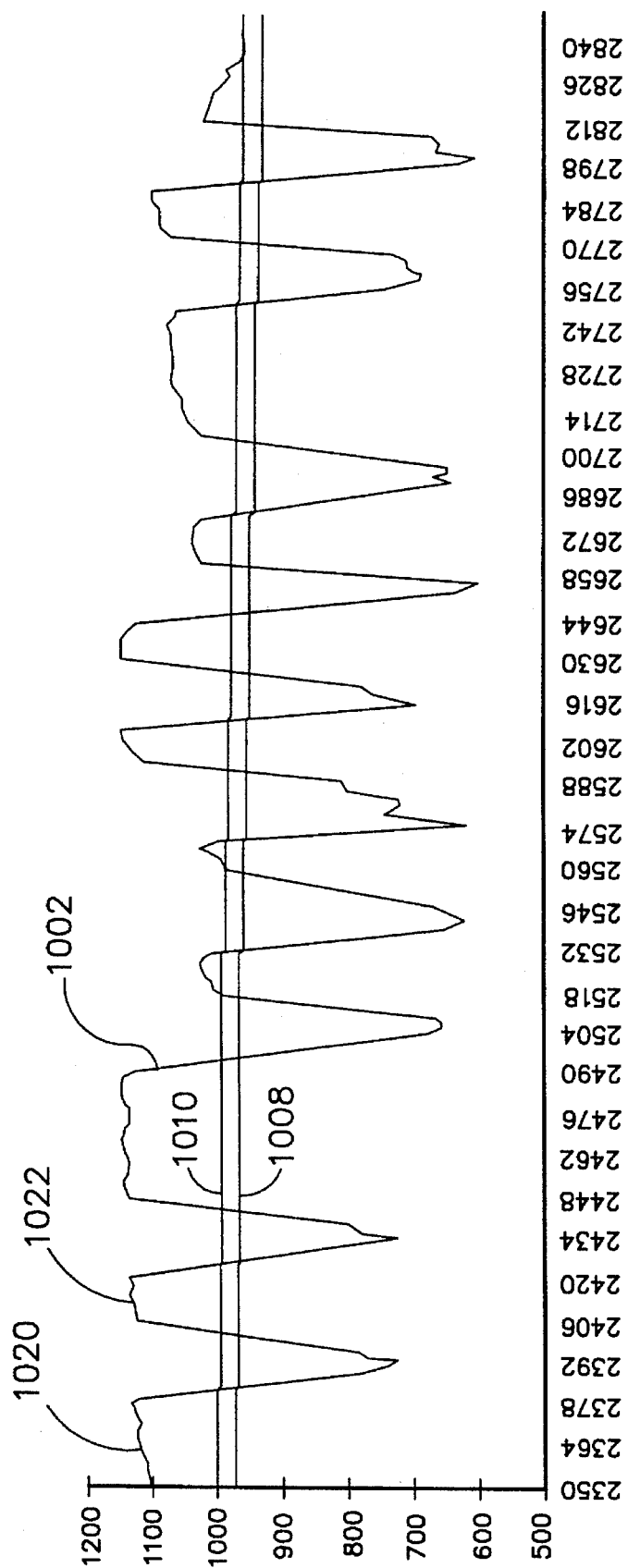
FIGS. 10 and 11 represent empirical data to illustrate conditions experienced by a photoelectric detector.

FIG. 10 shows a representation of actual empirical data that illustrates the reaction of the present invention to a gradual decrease in light intensity received by the light sensitive device. The actual signal 1002 is shown in a decreasing mode as a result of a gradual decrease in light intensity. The first threshold magnitude 1008 is illustrated as decreasing in reaction to this phenomenon. The second threshold 1010 is calculated as a function of the first threshold 1008. Although many specific algorithmic approaches can be used in alternative embodiments of the present invention, one particular technique includes the steps of taking individual maximum values for each peak region of signal 1002. For example, a maximum value can be determined for the region identified by reference numeral 1020, another maximum value can be determined for the region identified by reference numeral 1022, and so on. These maximum values can be stored in an array and each newly determined maximum value can be added to the array with the oldest entry being removed. This permits a moving average to be determined as new peak regions are encountered. The number of elements in the array can be, for example, 10. However, depending on the magnitude of noise level and the required response of the system other array sizes can be used. In FIG. 10, the first and second threshold magnitudes, 1008 and 1010, can be seen to have a step-shaped appearance. This results from the changes in the first and second threshold magnitudes that are made by the present invention as a function of the changes in the maximum values determined during the peak regions when no bottle was obstructing the light beam. FIG. 10 is intended to represent a gradual change in the light intensity provided by the light source to the light sensitive component. The information contained in FIG. 10 is empirical and derived from an experimental operation of the present invention. It should therefore be understood that the changes in light intensity shown in FIG. 10 are artificial and were induced for purposes of demonstrating the operation of the present invention.

With continued reference to FIG. 10, the changes in light intensity, although decreasing with time, are not sufficient to actually cause a bottle to be missed. As a result, the operation represented in FIG. 10 successfully monitored the presence of all the bottles passing through the light beam because of its continual adjustment of the first and second thresholds. Although FIG. 10 only shows decreases in the first and second thresholds, it should be clearly understood that it could also adjust to gradual increases in the light intensity.

Figure 11:
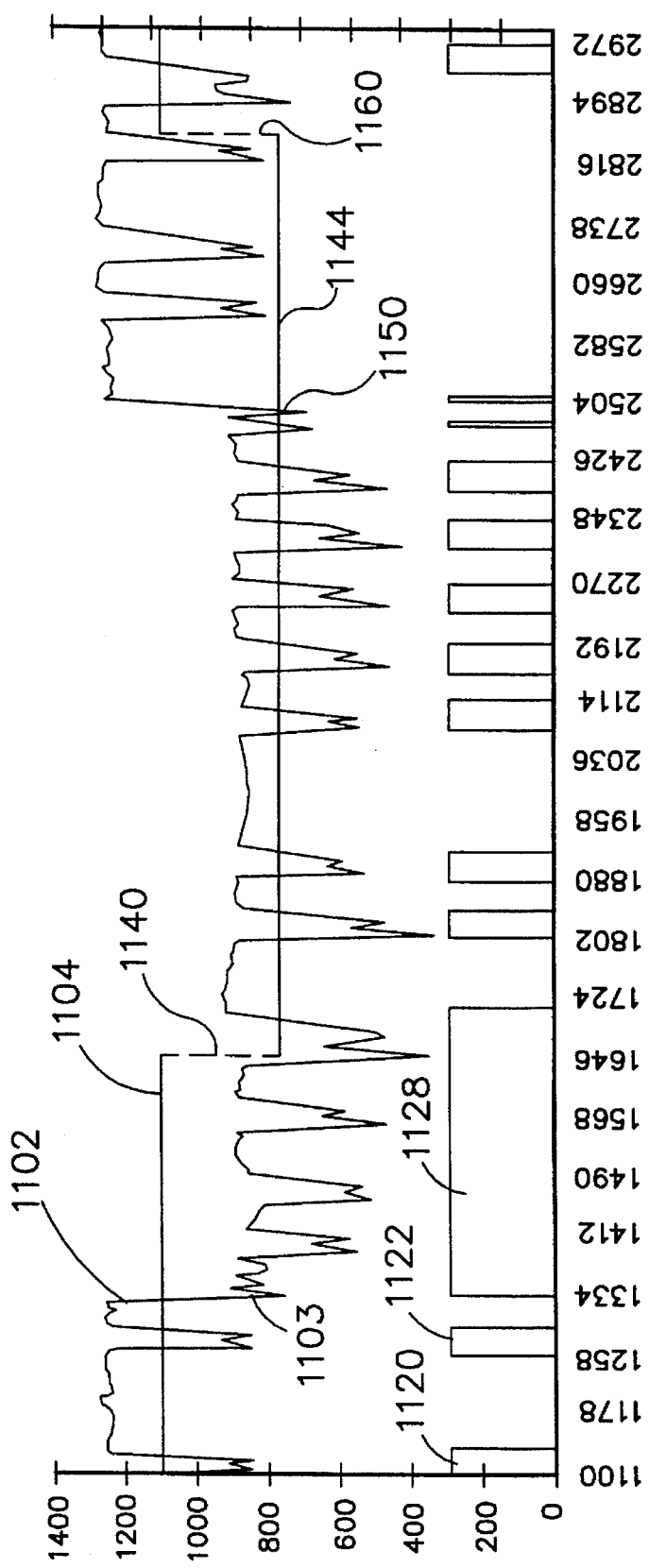

FIG. 11 illustrates the reaction of the present invention to a sudden large change in light intensity. This capability of the present invention will be described in greater detail below in conjunction with the flow charts. FIG. 11 is intended to show an alternative function of the present invention. In contradistinction to the situation represented in FIG. 10, FIG. 11 shows an example of how the present invention reacts to a sudden large decrease in light intensity. In comparing FIGS. 10 and 11, it should be understood that the changes shown in FIG. 10 could occur as a result of a gradually aging light emitting diode, a gradual increase in the particulate matter in the air or a gradual build up of water spray on either the retroreflector or the lenses. The situation shown in FIG. 11 is much more drastic than that and could represent the sudden deposition of water or oil on the mirror. Alternatively, it could represent a sudden misalignment of the retroreflector to an angle that only partially reflects the light back to the light receiving element. Regardless of the cause, it can be seen that the signal 1102 experiences a sudden decrease in intensity in the region identified by reference numeral 1103. Following that incident, the light signal never achieves the magnitude of threshold 1104. Therefore, no gap between bottles can be identified. If this situation arises, the algorithm described above in conjunction with FIG. 10 would not be able to function in the way that is was intended. Since the gaps between the bottles are used in the general approach of the present invention to accommodate gradual changes in light intensity, the lack of any indication that a bottle has pasted through the beam would drastically inhibit the ability of that type of algorithm to respond to the situation shown in FIG. 11. Instead, as described in conjunction with the flow charts of the present invention, the algorithm reacts to the situation in FIG. 11 as a function of time over which no bottle trailing edge is experienced. When the leading edge of an object is detected, the sensor begins to measure the time. During which the object remains in the status of a bottle being present. It compares that time period with a characteristic time period representing the time during which a bottle is typically in the light path. This characteristic time is obtained by a moving average of the number of time periods during which an object passes by and is updated after each object passes through the light beam. In other words, the present invention maintains a historical record of the previous preselected number of occurrences of objects and the typical time during which the object blocks the beam. If the current time period is longer than the characteristic time period by a preselected magnitude (e.g. four times as long), the sensor will switch into a self recovery routine as described in FIG. 14. In this portion of the routine, the sensor will not only compare the receiving signal with the threshold magnitude, but also search for contrast. The contrast is obtained by searching maximum and minimum values of the received signals and then calculating a contrast value which is determined by subtracting the minimum value from the maximum value and dividing the result by the maximum value. A transparent glass or plastic bottle can create a light intensity contrast of approximately 28 percent between the light intensity value when it is present in the light path and the light intensity value when it is absent from the light path. In other words, the light intensity received by the light sensitive component is expected to be decreased by approximately 28 percent when a bottle is in the path of the light beam. A predetermined value can be used to compare the calculated contrast to determine whether or not the contrast value is high enough to characterize an object. If the signal received by the light sensitive component never crosses the threshold, but the calculated contrast is high enough to characterize an object such as a transparent bottle, the sensor will reset its reference to the maximum value stored during the calculation of the contrast and then recalculate the threshold magnitudes according to the reference value. The actual condition shown in FIG. 11 illustrates a circumstance where, after detecting a blockage of light continuously for as long as four times the normal time period of a typical bottle blocking the light path, the sensor switches into the self recovery mode of operation. After one or two bottles pass through the light beam, as represented in the empirical situation shown in FIG. 11, the sensor found the contrast value and determined that the contrast during the period between pulse 1568 and pulse 1670 represented an actual object passing through the light beam. It then reset the threshold to that identified by reference numeral 1144 according to the maximum value obtained immediately prior to that change. A sensor made in accordance with the present invention can also switch into self recovery mode if it does not detect an object for a certain period of time. This period of time can be four times the typical bottle width time period. This is represented in FIG. 11 in the time period immediately preceding the change represented by reference numeral 1160. In other words, during the time period between pulse 2520 and pulse 2820, no bottle was sensed because the light intensity never dropped to a value less than threshold magnitude 1144.

Another use of the time period representing a typical bottle passing through the light beam is in the normal operation algorithm even when the system is not in a self recovery mode. When bottles, or other transparent objects, are close to each other as they pass through the light beam, the maximum value of light intensity received by the light sensitive component during the period when the light beam passes between bottles does not always return to an expected peak value because the bottles on both sides of the gap may partially block the beam. The time period of a typical bottle can be used to determine if the gap is large enough to recalculate the threshold. Depending on the beam width and the bottle size, a criterion can be set for a proper gap that ensures a desired true maximum as a function of the stored time period of a typical bottle. If the gap is smaller than this criterion, no new threshold is calculated.

With continued reference to FIG. 11, it can be seen although signals are properly provided, as identified by reference numerals 1120 and 1122, the signal identified by reference numeral 1128 does not terminate properly and approximately four bottles are missed because of the existence of the single improper signal 1128. However, as shown in the flow charts of the present invention which will be described in greater detail below, the magnitude of threshold 1104 changes at the point in time identified by reference numeral 1140 and a new magnitude 1144 is used from that point on. At the point identified by reference numeral 1150, a sudden increase is experienced in light intensity and the algorithm of the present invention responds to that sudden increase with the change identified by reference numeral 1160. It should be understood that the situation shown in FIG. 11 is empirical and was derived through an artificial manipulation of the light intensity during a trial run of the present invention.

In several of the Figures, the horizontal and vertical axes contain numerical values that are not specifically identified by name. For example, FIG. 10 has a vertical axis that ranges in magnitude from 500 to 1200 while FIG. 11 has a vertical axis that ranges in magnitude from 0 to 1400. These numbers represent digital values obtained from an analog-to-digital converter associated with several other components in a prototype model of the present invention. The vertical axes in the Figures therefore represent a relative light intensity indication, but the absolute numbers used in the figures are not, in themselves, relevant units of light intensity. Similarly, the horizontal axes in the figures represent the passage of time and are associated with numerical values. These numerical values are actually pulse numbers taken during prototype testing procedures. For example, in FIG. 10 the illustration shows the pattern of the signal 1002 and the first and second thresholds between the occurrence of light pulse 2350 and light pulse 2840. In other words, 490 light pulses occurred during the time sequence shown in FIG. 10. The illustration in FIG. 10 was selectively taken from a test run of approximately 8000 pulses and was chosen for its illustrative purposes. FIG. 11, on the other hand, represents the changes in the illustrated values taken between pulses 1100 and 2972. As in the situation relating to FIG. 10, the representation in FIG. 11 was selected from a total prototype test run of greater than 5000 pulses.

Figure 12A:
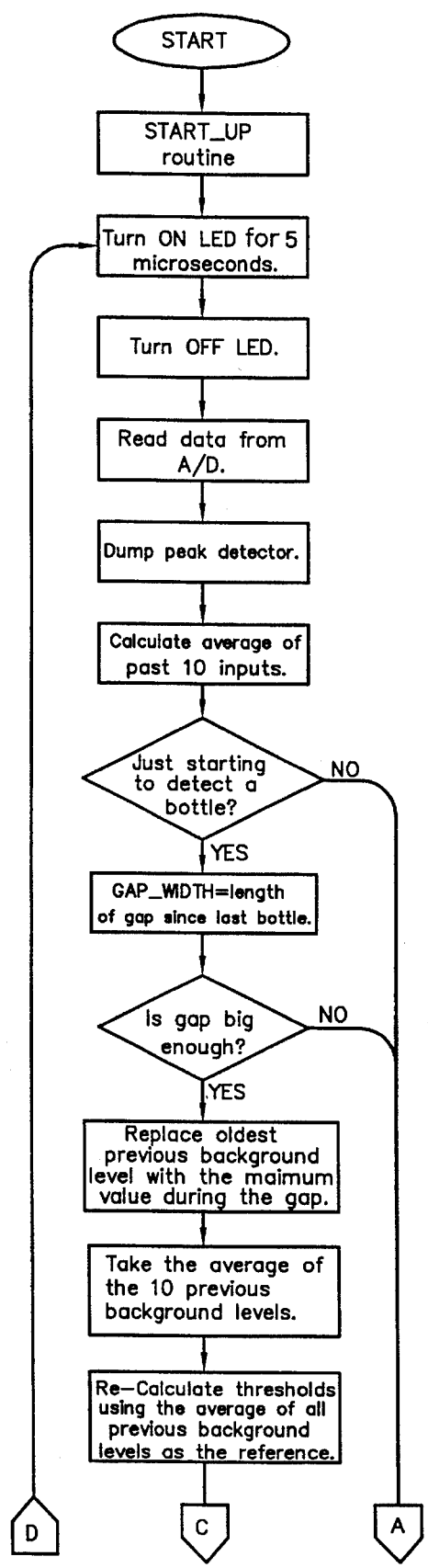
FIGS. 12A and 12B show a flow chart of the main routine used in a preferred embodiment of the present invention.
Figure 12B:
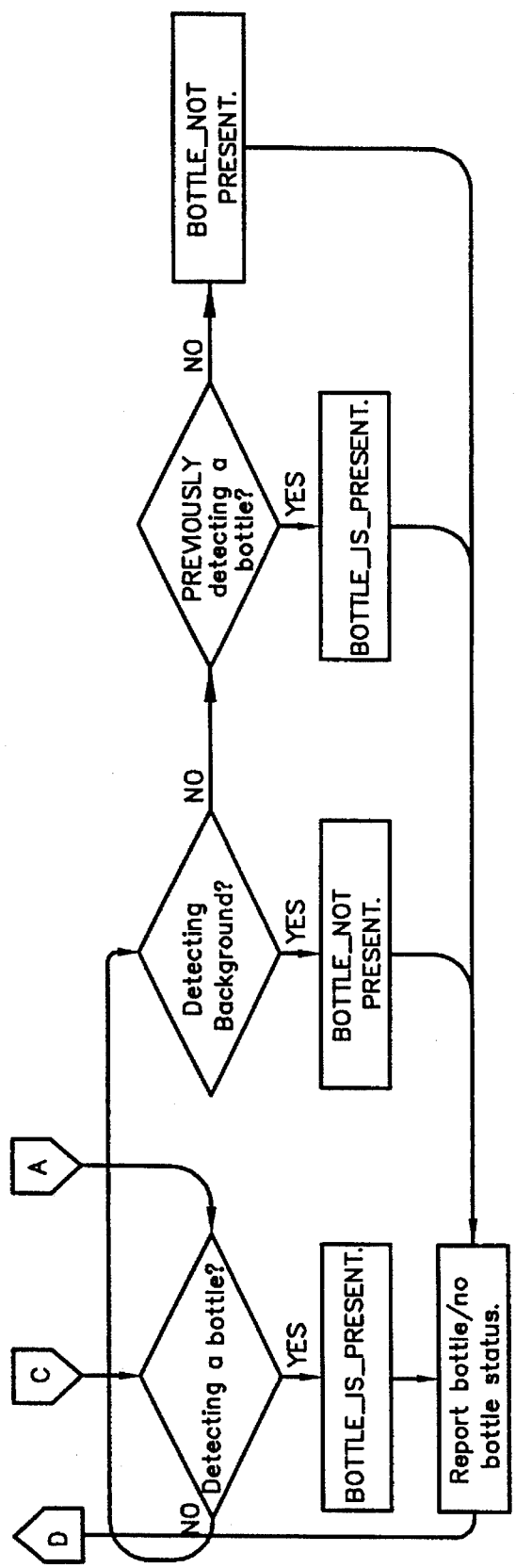
Figure 13A:
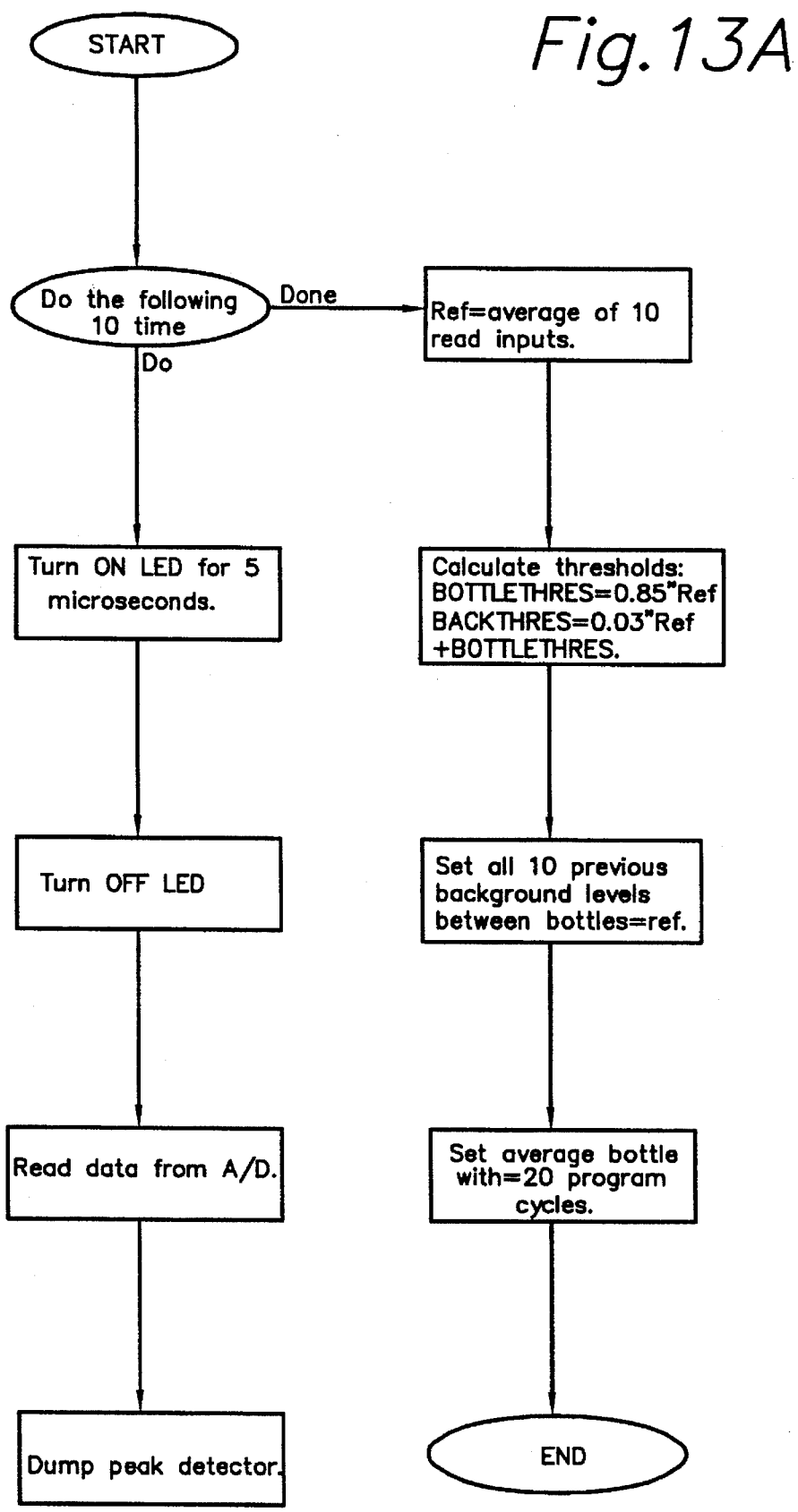
FIG. 13A is a start up routine used by the present invention.

The flow charts in the figures show the logical sequence followed by the present invention. The main program flow chart, shown in FIGS. 12A and 12B calls various subroutines, depending on the current situation, and continues to cycle. A particularly preferred embodiment of the present invention incorporates a microprocessor in which a control program performs the steps represented by the flow charts. The initial portion of the flow chart shows a start-up routine being initiated during which 10 input values are read and an average value of the 10 inputs is used to create 10 identical average value numbers. This is shown in FIG. 13A. The first and second thresholds are calculated as a result of these average values. It should be understood that this portion of the flow charts represents the initial start-up when no bottles are present in the light path. Therefore, the average values described in the flow chart are actually representative of the maximum values A2, A3 and A4 as described above during an actual run of the system with clear bottles. The initial characteristic time period "bottle width" that represents the time during which an object is typically in the path, is also set. When this start up routine is complete, the program main begins to cycle by reading the input and then averaging the last ten inputs. The examination of the gap width time determines whether the period of time when no bottle is present is too short compared with a preselected value such as a quarter of a bottle width. If the gap width time is too short, the new maximum value will be ignored and no new threshold will be calculated. This is done to prevent the condition when bottles are too close to each other.

The main flow chart determines if a leading edge of a bottle is detected, if a bottle_not_present condition is continuously detected, if a trailing edge of a bottle is detected or if a bottle is presently passing through the light beam. The actions taken, based on these four possibilities, are illustrated in the flow chart. The program continues to loop while it monitors the status of the received light signal based on the current situation of the light beam. In other words, the program continues to remember whether a bottle is considered passing through the light beam or not then and reacts to changes in the light signal based on this condition.

Figure 13B:
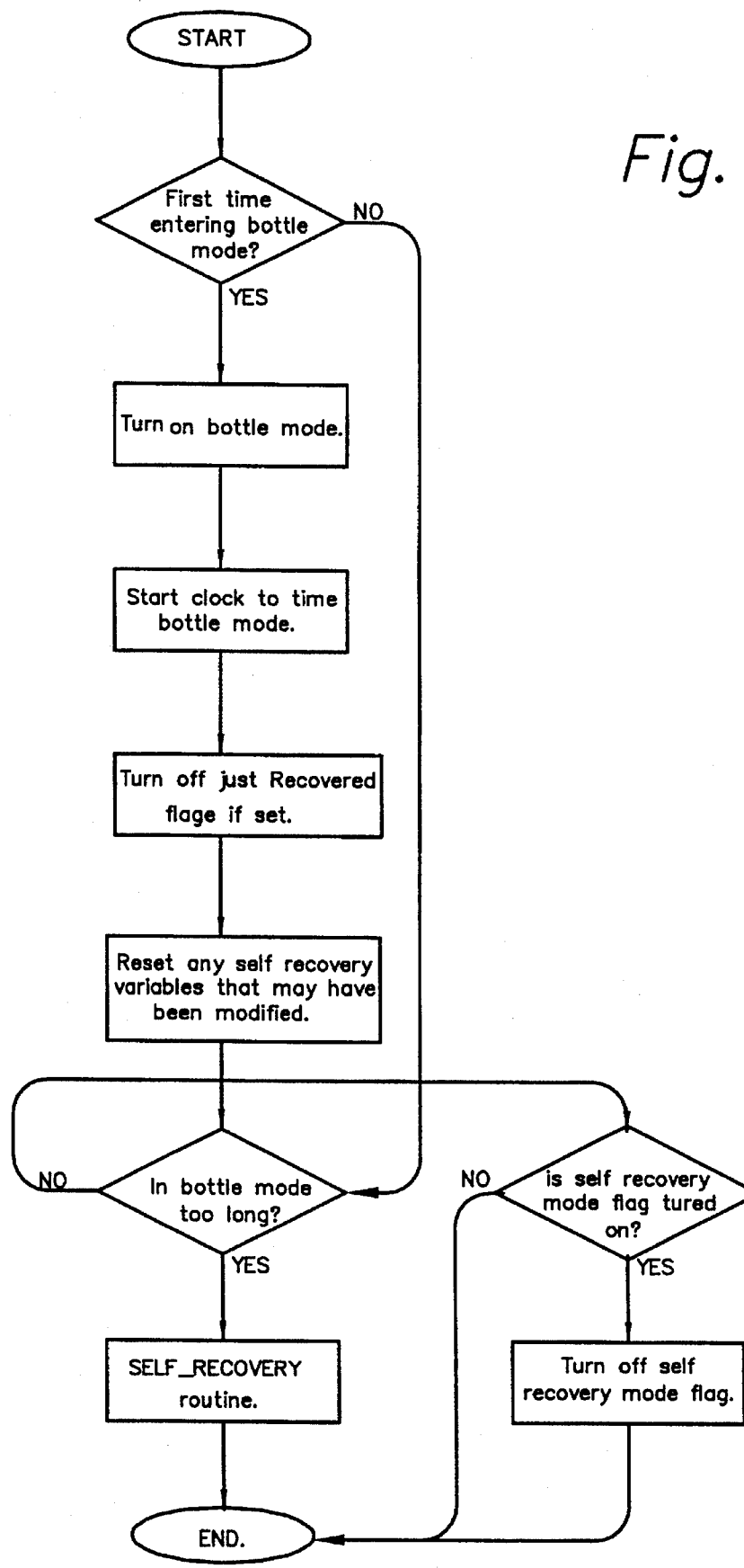
FIG. 13B and 13C show subroutines that are used during the "bottle present" and "bottle not present" situations.
Figure 13C:
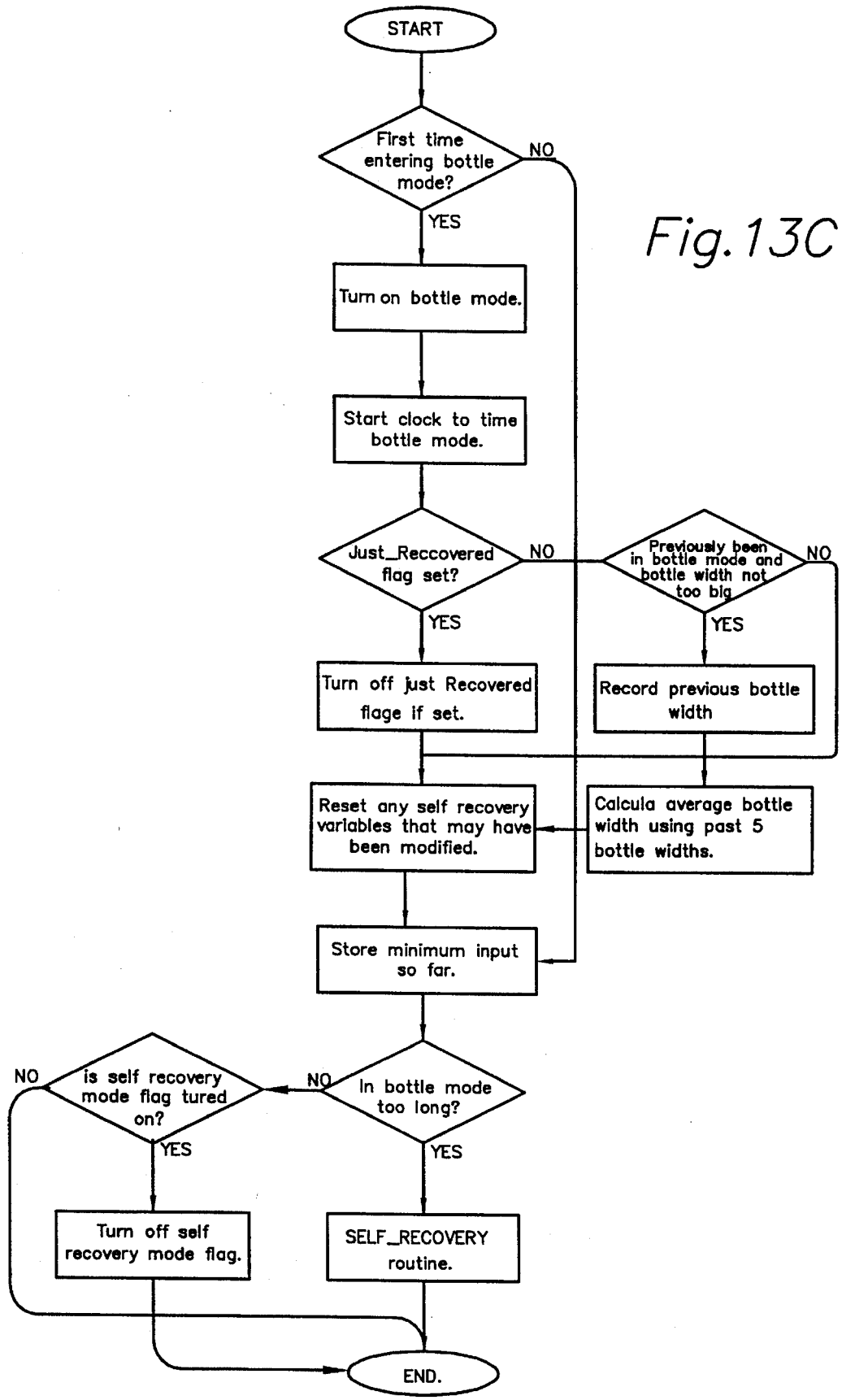
Figure 14A:
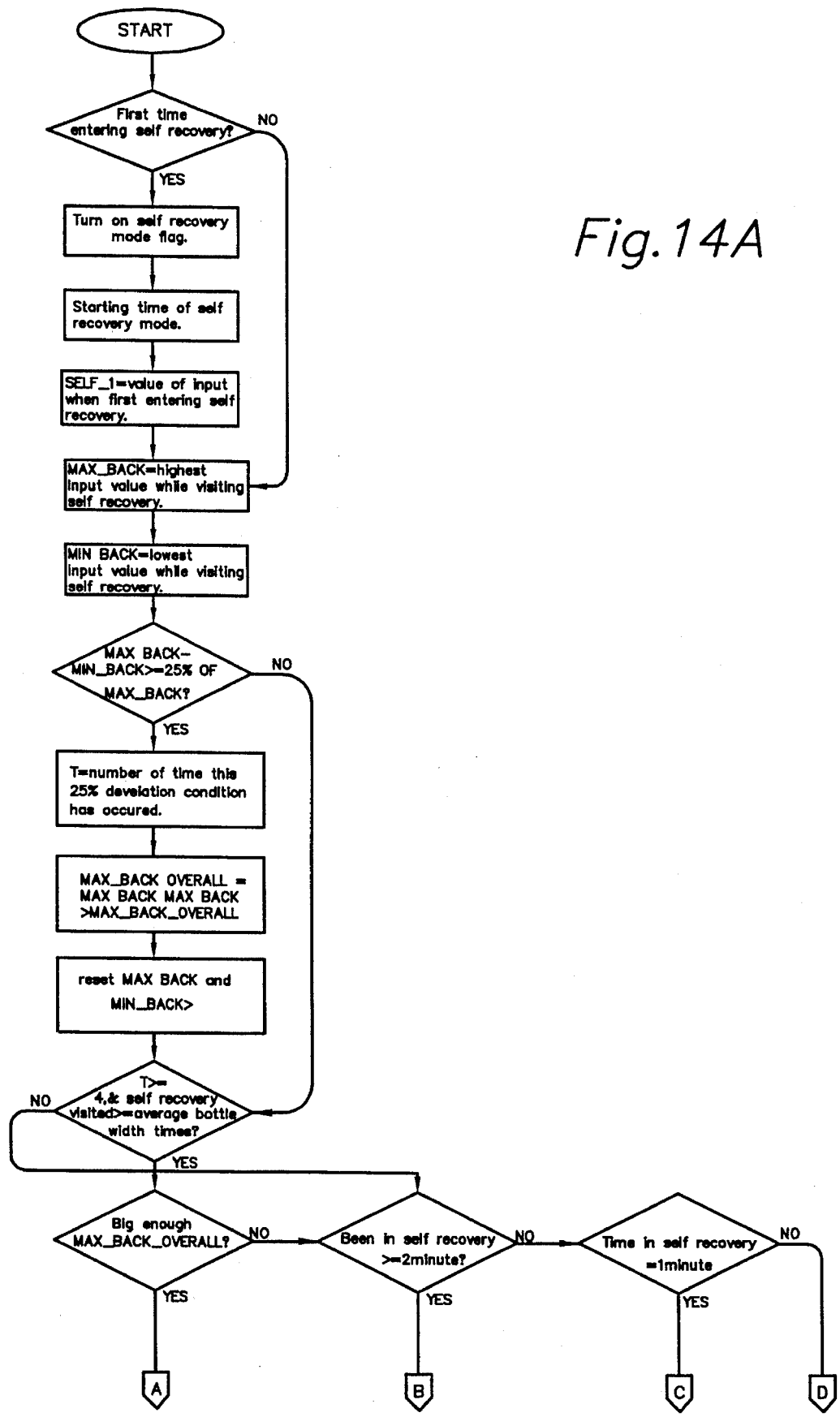
FIGS. 14A and 14B show a flow chart of the routine which operates during the self recovery mode of the present invention.
Figure 14B:
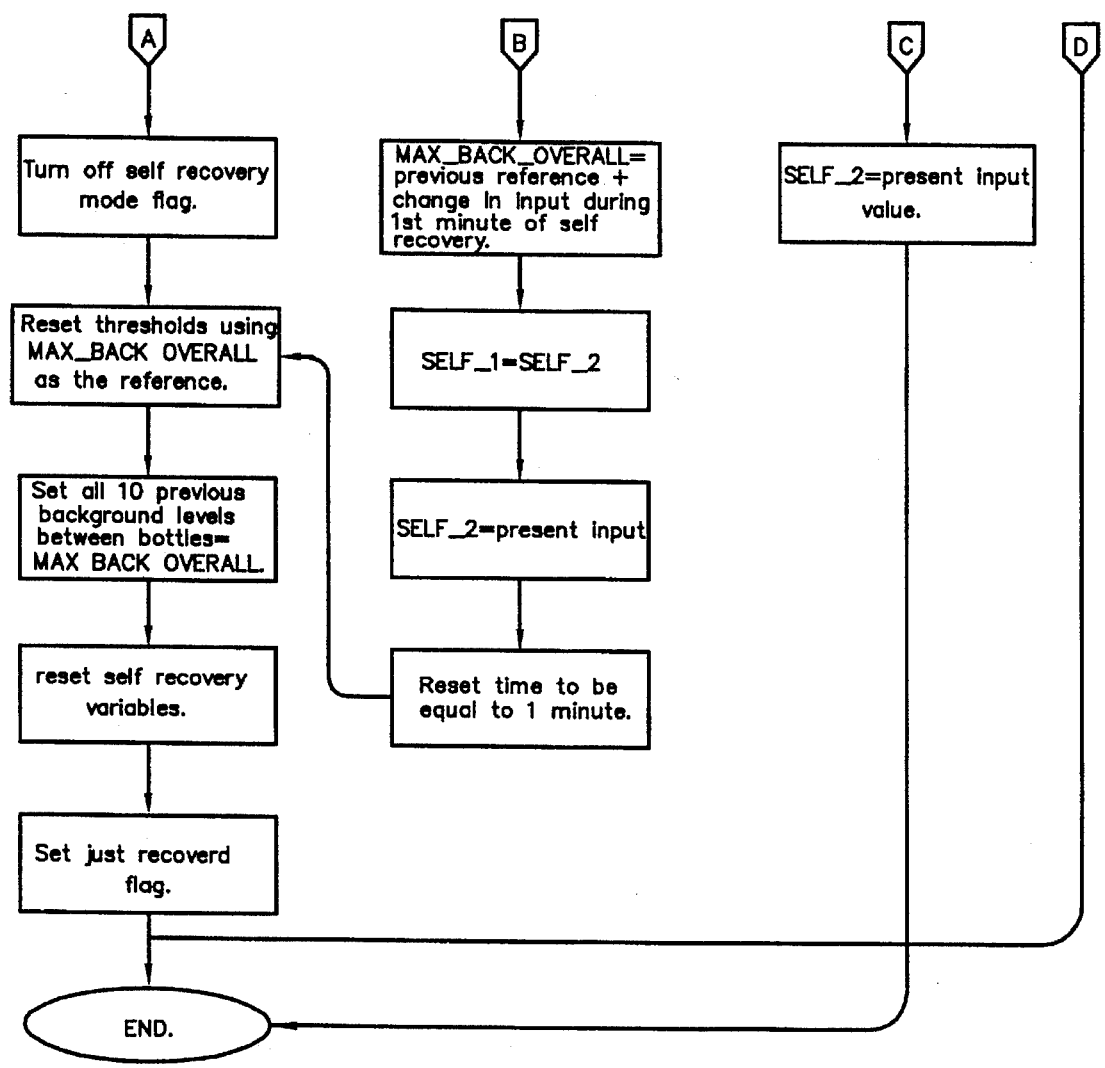

The basic architecture of the computer algorithm, as represented by the flow charts of the figures, comprises a main routine that continues to cycle and call other routines during the operation of the present invention. The main portion of the algorithm is illustrated in FIGS. 12A and 12B. In the initial portion of the flow chart in FIG. 12A, the START UP subroutine is called. The START UP subroutine is illustrated in FIG. 13A. In FIG. 12B, the main routine is shown as calling two subroutines, based on whether a bottle is present or a bottle is not present. Those subroutines are shown in FIGS. 13B and 13C. The self recovery mode of the present invention, which reacts when sudden large changes are experienced in the intensity of light received by the light sensitive component, is illustrated in FIGS. 14A and 14B.

When the program initially enters the self recovery mode, it starts a counting clock and stores the current signal value as self_1. It continues to search for, and stores, maximum and minimum values. Using the maximum and minimum values, it calculates the contrast value as described above and compares it with a preselected value which can be, for example, set to 0.25. To ensure a desired contrast that represents an object, at least a predetermined number of independent contrast values (e.g. four as shown in the flow chart) have to be found which satisfy the contrast criterion in at least one time period of bottle width. If the above conditions are satisfied, the largest value obtained in the independent searches for contrast is used as a new reference and new thresholds are calculated accordingly. This results in a self recovery. If an insufficient number of contrasts are found during a preselected period of time (e.g. one minute) during the self recovery mode, the signal value at the end of that period (e.g. one minute) is stored as self_2. If, after another preselected time period (e.g. one minute), no sufficient number of contrasts are found, the program will shift the reference by the difference of self_2 minus self_1. That is, at the end of a preselected time period after entering the self recovery mode, the program floats the reference value by the difference between the signal level at the middle point of the time period and the signal value at the beginning of the time period. New thresholds are then calculated accordingly. The clock is then set back to the middle point of the time period with self_1 updated with self_2. This allows the program to continue to float the reference repeatedly as described above. This feature of the present invention compensates for changes when no bottle is passing through the light beam for a long period of time or when a bottle is stopped in front of the sensor for a long period of time.

Figure 15:
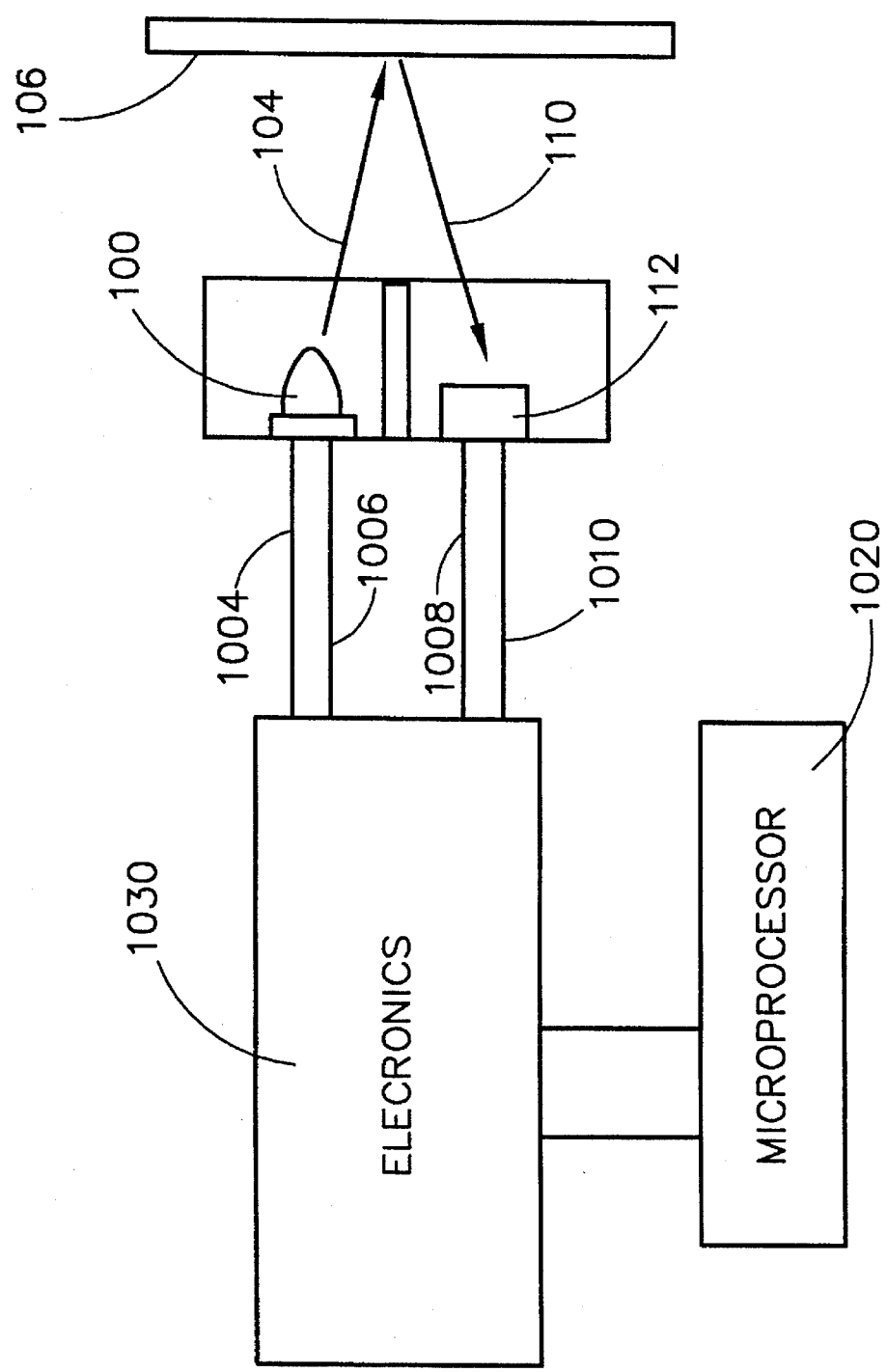
FIG. 15 is a schematic illustration of the circuit of the present invention.

FIG. 15 shows a schematic illustration of the circuit used to provide the functions of the present invention. A light source 100 and a light sensitive device 112 are provided in a housing. A reflector 106 is used to receive a light beam 104 and reflect it to provide a reflected beam 110. The light source 100, which can be a light emitting diode, is connected by lines 1004 and 1006 to the appropriate electronics to provide a pulsed energization of the light source 100. The light sensitive device 112 is connected by lines 1008 and 1010 to the electronics to provide a signal representing the intensity of light received from the reflected beam 110. A microprocessor 1020 is used to process the signals and perform the actions represented by the flow charts described above. The electronics 1030 will be described in greater detail below.

Figure 16:
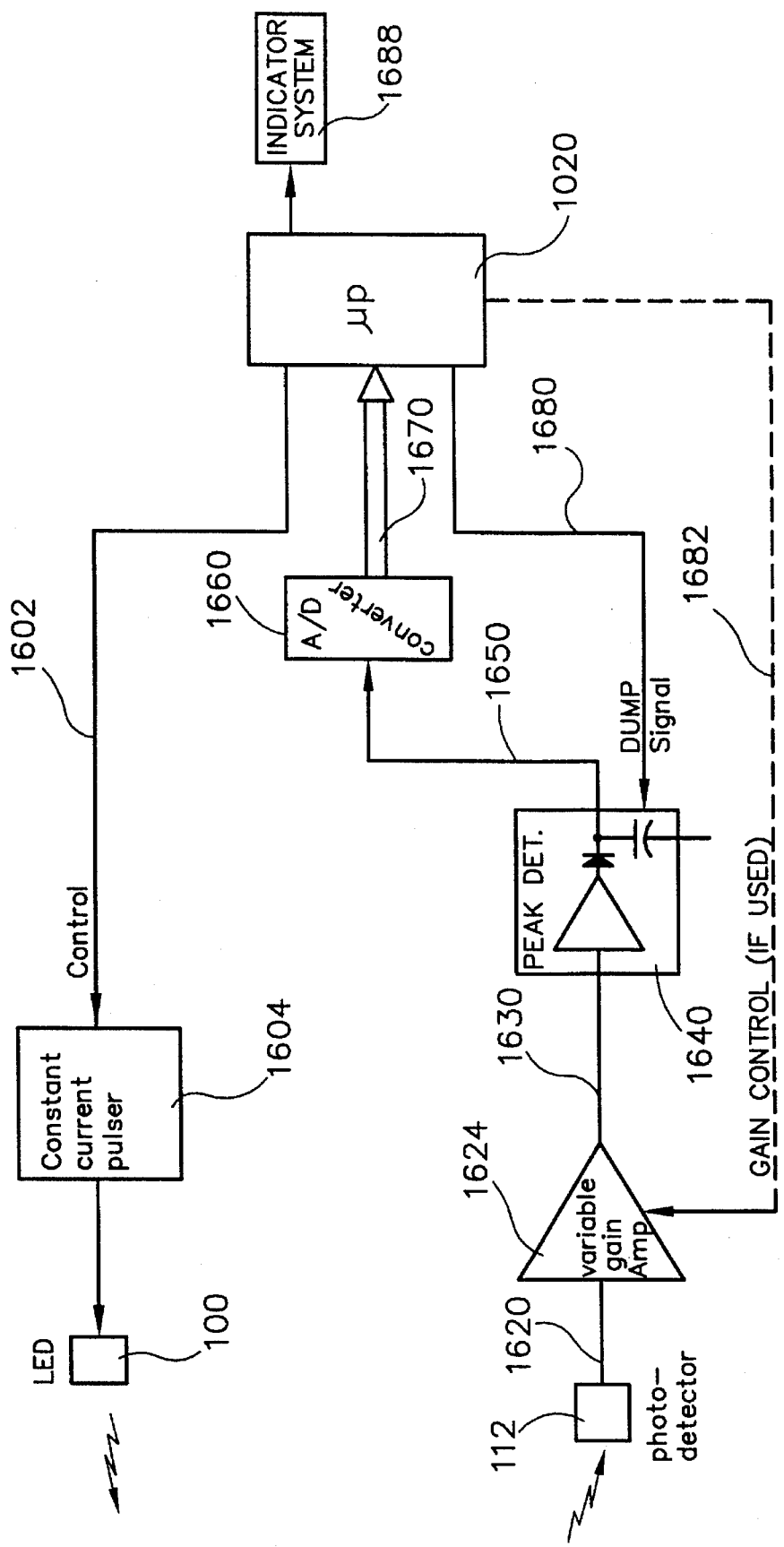
FIG. 16 is a more detailed configuration of the circuit of FIG. 15.

FIG. 16 is a schematic circuit representation of the present invention. It is slightly more detailed than the illustration of FIG. 15. The microprocessor 1020 provides a control signal 1602 to a constant current pulsar 1604. The pulsar 1604 provides a timed output pulse signal 1610 to a light emitting diode 100. The return pulses, whether reflected by a retroreflector or received by a separate photosensitive device in an individual housing, is received by a photodetector 112. The signal 1620 is provided to an amplifier 1624. The amplified signal 1630 is received by a peak detector 1640. The peak detector, in the manner generally described above, provides the magnitude of the peak signal value on line 1650 to an analog-to-digital converter 1660. The digital version of the peak magnitude is provided to the microprocessor 1020 as indicated by reference numeral 1670. If the pulse duration of the light is longer than the conversion time of the analog-to-digital converter, the peak detector is not required by the present invention. The operation of the peak detector 1640 is controlled by a signal 1680 from the microprocessor 1020. The peak value of the last pulse is deleted after it is converted so that each pulse value is independent of the last pulse. Also, the floating reference rate of change is independent of the peak detector. As represented by dashed line 1682, the microprocessor can be provided with a means to control the gain of the variable gain amplifier 1624 if this is necessary. When the microprocessor performs the steps described in conjunction with the flow charts, it is able to detect the presence and absence of a bottle passing through the beam of light. In order to provide a recognizable signal that a bottle has past through the path of the light beam, a indicator system 1688 is provided. It should be understood that the specific arrangement shown in FIG. 16 is not a limitation to the present invention. The indicator system 1688, for example, could be as simple as a light signal or, in a preferred embodiment of the present invention, could provide output signals that are receivable by other apparatus that maintains a bottle count or monitors the speed of the moving bottles as they pass through the light beam. The level of sophistication of a system incorporated in the present invention is variable depending on the requirements of the system.

With reference to FIGS. 1 and 2, it should be understood that many applications of photoelectric sensors incorporate a polarizer that is disposed between the lenses, 114 and 116, and the retroreflector 106. In many cases, a circular polarizer is used in order to remove the possibility that light reflected back from a mirror surface of an object to be detected can provide sufficient signal to the light receiving component to appear to be reflected light from the retroreflector 106. Photoelectric sensors might not detect an object when the object is blocking the path of the light beam and therefore reducing the received signals below a threshold magnitude. For transparent objects this type of signal reduction is primarily caused by specular reflection at the object surfaces. However, in retroreflective configurations, the object may reflect the light beam directly back to the receiver of the sensor. Depending on the reflectivity of the object surface and on the distance between the object and the receiver, the decrease in the received signal may be extremely small or, in some cases, the received light signal might even be increased as a result of the reflection of the object itself back to the light receiver. In order to reject the specular reflection from an object so that the only possible effect when an object passes through the light beam is to block the beam from returning to the light receiver, a circular polarizer or two linear polarizers can be used. This is done to make sure that a blockage of the light beam results in a loss in light intensity received by the light sensitive component. The circular polarizer or the two linear polarizers are typically disposed in front of the collimating and focusing lens, such as lenses 114 and 116 in FIGS. 1 and 2. For example, one circular polarizer can be mounted in front of both the collimating lens and the focusing lens. This type of polarizer will reject any reflected light that is emitted by the emitter from reaching the light receiver if the reflection does not change the state of polarization. Specular reflection does not change the polarization state and, therefore, it will be rejected by the polarizer. On the other hand, a retroreflector can be used to reflect the light back to the receiver since the retroreflector rotates the polarization state. One type of retroreflector that can be used for these purposes is a corner cube type retroreflector. The use of a polarizer and a retroreflector is well known to those skilled in the art.

Although the present invention has been described in significant detail and illustrated with particular specificity to disclose a preferred embodiment of the present invention, it should be understood that alternative embodiments are within its scope. The particular numbers and values used to describe the present invention are not limiting and alternative values could be used. In addition, the particular times when the thresholds are updated in response to the light signal are not limiting to the present invention.

The embodiments of the invention in which an exclusive property or right is claimed are defined as follows:

1. A sensor, comprising:

a radiation source;

a radiation sensitive device, said radiation sensitive device providing a first signal representative of an intensity of radiation imposed on said radiation sensitive device, said radiation sensitive device being disposed to receive a beam of radiation from said radiation source;

means for comparing said first signal to a first threshold magnitude in order to detect the presence of an object in the path of said beam of radiation;

first means connected in signal communication with said radiation sensitive device for determining an updated value of said first threshold magnitude as a function of the maximum value of a magnitude of said intensity of radiation imposed on said radiation sensitive device during a first preselected period of time;

means for deactivating said first determining means during a second preselected period of time; and means for replacing a previous value of said first threshold magnitude with said updated value of said first threshold magnitude upon the detection of said object in the path of said beam of radiation.

2. The sensor of claim 1, further comprising:

means for providing a second signal when said first signal achieves a first relationship with said first threshold magnitude.

3. The sensor of claim 1, further comprising:

second means for determining a second threshold magnitude as a function of said first threshold magnitude.

4. The sensor of claim 3, wherein:

said first signal is compared to said first threshold magnitude to detect a leading edge of said object; and said first signal is compared to said second threshold magnitude to detect a trailing edge of said object.

5. The sensor of claim 1, wherein:

said radiation is light.

6. The sensor of claim 1, further comprising:

a reflector disposed to receive said beam of radiation from said radiation source and reflect said beam of radiation toward said radiation sensitive device.

7. A photoelectric sensor, comprising:

a light source;

a light sensitive device, said light sensitive device providing a first signal representative of an intensity of light imposed on said light sensitive device, said light sensitive device being disposed to receive a beam of light from said light source;

means for comparing said first signal to a first threshold magnitude in order to detect the presence of an object in the path of said beam of light;

first means connected in signal communication with said light sensitive device for determining an updated value of said first threshold magnitude as a function of the maximum value of a magnitude of said intensity of light imposed on said light sensitive device during a first preselected period of time;

means for deactivating said first determining means during a second preselected period of time;

means for replacing a previous value of said first threshold magnitude with said updated value of said first threshold magnitude upon the detection of said object in the path of said beam of light; and means for providing a second signal when said first signal achieves a first relationship with said first threshold magnitude.

8. The sensor of claim 7, further comprising:

second means for determining a second threshold magnitude as a function of said first threshold magnitude.

9. The sensor of claim 8, wherein:

said first signal is compared to said first threshold magnitude to detect a leading edge of said object; and said first signal is compared to said second threshold magnitude to detect a trailing edge of said object.

10. The sensor of claim 9, further comprising:

a reflector disposed to receive said beam of light from said light source and reflect said beam of light toward said light sensitive device.

11. The sensor of claim 9, wherein:

said first determining means comprises a microprocessor.

12. A photoelectric sensor, comprising:

a light source;

a light sensitive device, said light sensitive device providing a first signal representative of an intensity of light imposed on said light sensitive device, said light sensitive device being disposed to receive a beam of light from said light source;

means for comparing said first signal to a first threshold magnitude in order to detect the presence of an object in the path of said beam of light;

first means connected in signal communication with said light sensitive device for determining an updated value of said first threshold magnitude as a function of the maximum value of a magnitude of said intensity of light imposed on said light sensitive device during a first preselected period of time;

means for deactivating said first determining means during a second preselected period of time;

means for replacing a previous value of said first threshold magnitude with said updated value of said first threshold magnitude upon the detection of said object in the path of said beam of light;

means for providing a second signal when said first signal achieves a first relationship with said first threshold magnitude; and second means for determining a second threshold magnitude as a function of said first threshold magnitude.

13. The sensor of claim 12, wherein:

said first signal is compared to said first threshold magnitude to detect a leading edge of said object; and said first signal is compared to said second threshold magnitude to detect a trailing edge of said object.

14. The sensor of claim 13, further comprising:

a reflector disposed to receive said beam of light from said light source and reflect said beam of light toward said light sensitive device.

\* \* \* \* \*